US009897612B2

(12) United States Patent
Diem et al.

(10) Patent No.: US 9,897,612 B2
(45) Date of Patent: Feb. 20, 2018

(54) FIBRONECTIN TYPE III REPEAT BASED PROTEIN SCAFFOLDS WITH ALTERNATIVE BINDING SURFACES

(71) Applicant: Janssen Biotech, Inc., Spring House, PA (US)

(72) Inventors: Michael Diem, Havertown, PA (US); Steven Jacobs, North Wales, PA (US)

(73) Assignee: Janssen Biotech, Inc., Horsham, PA (US)

(*) Notice: Subject to any disclaimer, the term of this patent is extended or adjusted under 35 U.S.C. 154(b) by 163 days.

(21) Appl. No.: 14/822,335

(22) Filed: Aug. 10, 2015

(65) Prior Publication Data

US 2016/0041182 A1 Feb. 11, 2016

Related U.S. Application Data

(62) Division of application No. 13/628,393, filed on Sep. 27, 2012, now Pat. No. 9,200,273.

(60) Provisional application No. 61/539,670, filed on Sep. 27, 2011.

(51) Int. Cl.

| | |
|---|---|
| ***C40B 30/04*** | (2006.01) |
| ***G01N 33/68*** | (2006.01) |
| ***C12N 15/10*** | (2006.01) |
| ***C40B 40/08*** | (2006.01) |
| ***C40B 50/06*** | (2006.01) |

(52) U.S. Cl.

CPC ..... *G01N 33/6845* (2013.01); *C12N 15/1044* (2013.01); *C40B 40/08* (2013.01); *C40B 50/06* (2013.01); *C40B 30/04* (2013.01); *G01N 2333/78* (2013.01)

(58) Field of Classification Search

None

See application file for complete search history.

(56) References Cited

U.S. PATENT DOCUMENTS

| | | | |
|---|---|---|---|
| 5,643,768 | A | 7/1997 | Kawasaki |
| 6,018,030 | A | 1/2000 | Ferrari et al. |
| 6,355,776 | B1 | 3/2002 | Ferrari et al. |
| 6,462,189 | B1 | 10/2002 | Koide |
| 6,521,427 | B1 | 2/2003 | Evans |
| 6,670,127 | B2 | 12/2003 | Evans |
| 6,673,901 | B2 | 1/2004 | Koide |
| 6,703,199 | B1 | 3/2004 | Koide |
| 6,818,418 | B1 | 11/2004 | Lipovsek |
| 6,846,655 | B1 | 6/2005 | Wagner et al. |

(Continued)

FOREIGN PATENT DOCUMENTS

| | | |
|---|---|---|
| EP | 1 137 941 B1 | 12/1998 |
| EP | 0 985 039 B1 | 3/2000 |

(Continued)

OTHER PUBLICATIONS

Teresa K. Atwood, "Genomics: The Babel of Bioinformatics," Science, 290(5491): 471-473 (2000).

(Continued)

*Primary Examiner* — Christian Boesen

(74) *Attorney, Agent, or Firm* — Eric Dichter

(57) ABSTRACT

Protein scaffolds and scaffold libraries based on a fibronectin type III (FN3) repeat with an alternative binding surface design, isolated nucleic acids encoding the protein scaffolds, vectors, host cells, and methods of making thereof are useful in the generation of therapeutic molecules and treatment and diagnosis of diseases and disorders.

7 Claims, 10 Drawing Sheets

(56) References Cited

U.S. PATENT DOCUMENTS

| | | | |
|---|---|---|---|
| 7,078,490 | B2 | 7/2006 | Koide |
| 7,115,396 | B2 | 10/2006 | Lipovsek et al. |
| 7,119,171 | B2 | 10/2006 | Koide |
| 7,153,661 | B2 | 12/2006 | Koide |
| 7,842,476 | B2 | 11/2010 | McGregor et al. |
| 8,278,419 | B2 | 10/2012 | Jacobs et al. |
| 2004/0259781 | A1 | 12/2004 | Chiquet-Ehrismann et al. |
| 2005/0255548 | A1 | 11/2005 | Lipovsek et al. |
| 2006/0040278 | A1 | 2/2006 | Cojocaru et al. |
| 2006/0246059 | A1 | 11/2006 | Lipovsek et al. |
| 2006/0270604 | A1 | 11/2006 | Lipovsek et al. |
| 2007/0148126 | A1 | 6/2007 | Chen et al. |
| 2007/0160533 | A1 | 7/2007 | Chen et al. |
| 2007/0184476 | A1 | 8/2007 | Hsieh et al. |
| 2008/0015339 | A1 | 1/2008 | Lipovsek et al. |
| 2008/0220049 | A1 | 9/2008 | Chen et al. |
| 2009/0176654 | A1 | 7/2009 | Cappuccilli et al. |
| 2010/0144601 | A1 | 6/2010 | Jacobs et al. |
| 2010/0216708 | A1 | 8/2010 | Jacobs et al. |
| 2010/0255056 | A1 | 10/2010 | Jacobs et al. |
| 2011/0038866 | A1 | 2/2011 | Hastewell et al. |
| 2011/0124527 | A1 | 5/2011 | Cappuccilli et al. |
| 2011/0274623 | A1 | 11/2011 | Jacobs |

FOREIGN PATENT DOCUMENTS

| | | | |
|---|---|---|---|
| EP | 1 266 025 | B1 | 12/2002 |
| WO | WO 01/64942 | A1 | 9/2001 |
| WO | WO 02/32925 | A2 | 4/2002 |
| WO | WO 03/104418 | A2 | 12/2003 |
| WO | WO 2004/029224 | A2 | 4/2004 |
| WO | WO 2004/058821 | A2 | 7/2004 |
| WO | WO 2007/085815 | A2 | 8/2007 |
| WO | WO 2008/079973 | A2 | 7/2008 |
| WO | WO 2008/156642 | A1 | 12/2008 |
| WO | WO 2009/023184 | A2 | 2/2009 |
| WO | WO 2009/058379 | A2 | 5/2009 |
| WO | WO 2009/086116 | A2 | 7/2009 |
| WO | WO 2009/133208 | A1 | 11/2009 |
| WO | WO 2010/051274 | A1 | 5/2010 |
| WO | WO 2010/060095 | A1 | 5/2010 |
| WO | WO 2011/005133 | A1 | 1/2011 |
| WO | WO 2012/016245 | A2 | 2/2012 |

OTHER PUBLICATIONS

Bass, et al., "Hormone Phage: An Enrichment Method for Variant Proteins with Altered Binding Properties," Proteins: Structure, Function, and Genetics, 8: 309-314 (1990).

Binz, et al., "High-affinity binders selected from designed ankyrin repeat proteins libraries," Nature Biotechnology, 22(5): 575-582 (2004).

Binz, et al., "Engineered proteins as specific binding reagents," Current Opinion in Biotechnology, 16: 459-469 (2005).

Bork, et al., "Proposed acquisition of an animal protein domain by bacteria," Proceedings of the National Academy of Science USA, 89: 8990-8994 (1992).

Clarke, et al., "Folding and Stability of a Fibronectin Type III Domain of Human Tenascin," Journal of Molecular Biology, 270: 771-778 (1997).

Dehouck, et al., "Fast and accurate predictions of protein stability changes upon mutations using statistical potentials and neural networks: PoPMuSiC-2.0," Bioinformatics, 25(19): 2537-2543 (2009).

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Dutta, et al., "High-affinity fragment complementation of a fibronectin type III domain and its application to stability enhancement," Protein Science, 14: 2838-2848 (2005).

Garrard, et al., "Selection of an anti-IGF-1 Fab from a Fab phage library created by mutagenesis of multiple CDR loops," Gene, 128: 103-109 (1993).

Getmanova, et al., "Antagonists to Human and Mouse Vascular Endothelial Growth Factor Receptor 2 Generated by Directed Protein Evolution In Vitro," Chemistry & Biology, 13: 549-556 (2006).

Hackel, et al., "Stability and CDR Composition Biases Enrich Binder Functionality Landscapes," Journal of Molecular Biology, 401: 84-96 (2010).

Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).

Hanes, et al., In vitro selection and evolution of functional proteins by using ribosome display, Proceedings of the National Academy of Science USA, 94: 4937-4942 (1997).

Helms, et al., "Destabilizing loop swaps in the CDRs of an immunoglobulin VL domain," Protein Science, 4: 2073-2081 (1995).

Jain, et al., "Designing Protein Denaturants: Synthetic Agents Induce Cytochrome c Unfolding at Low concentrations and Stoichiometries," Agnew. Chem., 114(4): 663-665 (2002).

Karatan, et al., "Molecular Recognition Properties of FN3 Monobodies that Bind the Src SH3 Domain," Chemistry & Biology, 11: 835-844 (2004).

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).

Koide, et al., Teaching an Old Scaffold New Tricks: Monobodies Constructed Using Alternative Surfaces of the FN3 Scaffold, Journal of Molecular Biology, 415: 393-405 (2012).

Koide, et al., "The Fibronectin Type III Domain as a Scaffold for Novel Binding Proteins," Journal of Molecular Biology, 284: 1141-1151 (1998).

Koide, et al., "High-affinity single-domain binding proteins with a binary-code interface," Proceedings of the National Academy of Science, 104(16): 6632-6637 (2007).

Kolvunen, et al., "Identification of Receptor Ligands with Phage Display Peptide Libraries," Journal of Nucleic Medicine, 40: 883-888 (1999).

Kunkel, et al., "Rapid and Efficient Site-Specific Mutagenesis without Phenotypic Selection," Methods Enzymology, 154: 367-382 (1987).

Irwin D. Kuntz, "Structure-based strategies for drug design and discovery," Science, 257(5073): 1078-1082 (1992).

Lehmann, et al., "Engineering proteins for thermostability: the use of sequence alignments versus rational design and directed evolution," Current Opinion in Biotechnology, 12: 371-375 (2001).

Lipovšek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).

Meinke, et al, "Cellulose-Binding Polypeptides from *Cellulomonas fimi*: Endoglucanase D (CenD), a Family A β-1,4-Gucanase," Journal of Bacteriology, 175(7): 1910-1918 (1993).

Miller, et al., "Ligand binding to proteins: the binding landscape model," Protein Science, 6(10): 2166-2179 (1997).

Odegrip, et al., "CIS display: In vitro selection of peptides from libraries of protein-DNA complexes," Proceedings of the National Academy of Science, 101(9): 2806-2810 (2004).

Olson, et al., "Design, expression, and stability of a diverse protein library based on the human fibronectin type III domain," Protein Science, 16: 476-484 (2007).

C.N. Pace, "Determination and Analysis of Urea and Guanidine Hydrochloride Denaturation Curves," Methods in Enzymology, 131: 266-280 (1986).

Parker, et al., "Antibody mimics based on human fibronectin type three domain engineered for thermostability and high-affinity binding to vascular endothelial growth factor receptor two," Protein Engineering, Design & Selection, 18(9): 435-444 (2005).

Reiss, et al., "Inhibition of platelet aggregation by grafting RGD and KGD sequences on the structural scaffold of small disulfide rich proteins," Platelets, 17(3): 153-157 (2006).

(56) References Cited

OTHER PUBLICATIONS

Roberts, et al., "RNA-peptide fusions for the in vitro selection of peptides and proteins," Proceedings of the National Academy of Science USA, 94: 12297-12302 (1997).
Siggers, et al., "Conformational Dynamics in Loop Swap Mutants of Homologous Fibronectin Type III Domains," Biophysical Journal, 93: 2447-2456 (2007).
Arne Skerra, "Engineered protein scaffolds for molecular recognition," Journal of Molecular Recognition, 13: 167-187 (2000).
Skolnick, et al., "From genes to protein structure and function: novel applications of computational approaches in the genomic era," Trends Biotechnology, 18(1):34-39 (2000).
Steiner, et al., "Efficient Selection of DARPins with Sub-nonomolar Affinities using SRP Phage Display," Journal of Molecular Biology, 382: 1211-1227 (2008).
Watanabe, et al., "Gene Cloning of Chitinase A1 from *Bacillus circulans* WL-12 Revealed Its Evolutionary Relationship to *Serratia* Chitinase and to the Type III Homology United of Fibronectin," The Journal of Biological Chemistry, 265 (26): 15659-15665 (1990).
Xu, et al., "Directed Evolution of High-Affinity Antibody Mimics Using mRNA Display," Chemistry & Biology, 9: 933-942 (2002).

Figure 3.

| | | A AB B BC | |
|---|---|---|---|
| TENCON27 | (1) | LPAPKNLVVSRVTEDSARLSWTAPDAAFDS | (30) |
| TCL14 | (1) | LPAPKNLVVSRVTEDSARLSWTAPDAAFDS | (30) |
| | | C CD D DE E | |
| TENCON27 | (31) | FLIQYQESEKVGEAIVLTVPGSERSYDLTG | (60) |
| TCL14 | (31) | FXIXYXEXXXXGEAIVLTVPGSERSYDLTG | (60) |
| | | EF F FG G | |
| TENCON27 | (61) | LKPGTEYTVSIYGVKGGHRSNPLSAIFTT | (89) |
| TCL14 | (61) | LKPGTEYXVXIXGVKGGXXSXPLSAIFTT | (89) |

Figure 4.

```
                        A          AB    B        BC
TENCON27    (1)    LPAPKNLVVSRVTEDSARLSWTAPDAAFDS        (30)
TCL15       (1)    LPAPKXLXVXXVXXXXAXLXWXAPDAAFDS        (30)

                      C         CD        D      DE   E
TENCON27    (31)   FLIQYQESEKVGEAIVLTVPGSERSYDLTG        (60)
TCL15       (31)   FLIQYQESEKVGEAIVLTVPGSERXYXLTG        (60)

                    EF       F           FG         G
TENCON27     (61)LKPGTEYTVSIYGVKGGHRSNPLSAIFTT         (89)
TCL15        (61)LKPGTEYTVSIYGVKGGHRSNPLSAIFTT         (89)
```

Figure 8.

```
                              A         AB    B      BC
Tencon27      (1)       LPAPKNLVVSRVTEDSARLSWTAPDAAFDS (30)
TCL14                  -LPAPKNLVVSRVTEDSARLSWTAPDAAFDS
Fibcon                 -LDAPTDLQVTNVTDTSITVSWTPPSATITG
FN10                   VSDVPRDLEVVAATPTSLLISWDAPAVTVRY
TN3                    --DAPSQIEVKDVTDTTALITWFKPLAEIDG
                          .* :: *   .*   :   ::*   *  .  .

                         C     CD      D      DE    E
Tencon27      (31)     FLIQYQESEKVGEAIVLTVPGSERSYDLTG (60)
TCL14                  FXIXYXEXXXXGEAIVLTVPGSERSYDLTG
Fibcon                 YXIXYXPXXXXGEPKELTVPPSSTSVTITG
FN10                   YXIXYXEXXXXSPVQEFTVPGSKSTATISG
TN3                    IXLXYXIXXXXGDRTTIDLTEDENQYSIGN
                        *:***  ****.     : :. ..     :  .

                       EF     F          FG         G
Tencon27      (61)     LKPGTEYTVSIYGV  KGG  HRSNPLSAIFTT(89)
TCL14                  LKPGTEYXVXIXGV--KGG--XXSXPLSAIFTT
Fibcon                 LTPGVEYXVXLXAL--KDN--XXSXPLVGTQTT
FN10                   LKPGVDYXIXVXAVTGRGDSPXXSXPISINYRT
TN3                    LKPDTEYXVXLXSR--RGD--XXSXPAKETFTT
                       *.*..:**:*:*.    :..    *         *
```

FIBRONECTIN TYPE III REPEAT BASED PROTEIN SCAFFOLDS WITH ALTERNATIVE BINDING SURFACES

CROSS REFERENCE TO RELATED APPLICATIONS

This application is a divisional of U.S. application Ser. No. 13/628,393, filed 27 Sep. 2012, now U.S. Pat. No. 9,200,273, granted 1 Dec. 2015, which claims priority to U.S. Provisional Application Ser. No. 61/539,670, filed 27 Sep. 2011, the entire contents of which are incorporated herein by reference in their entireties.

FIELD OF THE INVENTION

The present invention relates to protein scaffolds and scaffold libraries based on a fibronectin type III (FN3) repeat with alternative binding surface designs. More particularly, the present invention is directed to FN3 scaffolds and libraries having concave binding sites formed by select beta-strands and loops.

BACKGROUND OF THE INVENTION

Monoclonal antibodies are the most widely used class of therapeutic proteins when high affinity and specificity for a target molecule are desired. However, non-antibody proteins having relatively defined three-dimensional structures that can be engineered to bind desired target molecules, commonly referred to as protein scaffolds, may have advantages over traditional antibodies due to their small size, lack of disulphide bonds, high stability, and ability to be expressed in prokaryotic hosts. These scaffolds typically contain one or more regions which are amenable to specific or random sequence variation, and such sequence randomization is often carried out to produce libraries of proteins from which desired products may be selected. Novel methods of purification are readily applied; scaffolds are easily conjugated to drugs/toxins, penetrate efficiently into tissues and can be formatted into multispecific binders (Binz and Pluckthun, *Curr Opin Biotechnol*, 16, 459-469, 2005; Skerra, *J Mol Recognit*, 13, 167-187, 2000).

One such protein scaffold is the fibronectin type III (FN3) domain identified in a multitude of proteins, having a characteristic tertiary structure with 6 loops connected by 7 beta strands. Three loops in particular, the FG, BC, and DE loops are structurally analogous to the complementarity determining regions (CDRs) of antibodies. These loops have been randomized to generate libraries of the FN3 domain scaffolds to successfully select specific binders to a number of different targets while retaining important biophysical properties (Getmanova et al., *Chem Biol*, 13, 549-556, 2006; Hackel et al., *J Mol Biol*, 381, 1238-1252, 2008; Karatan et al., *Chem Biol*, 11, 835-844, 2004; Koide et al., *J Mol Biol*, 284, 1141-1151, 1998; Koide et al., *Proc Natl Acad Sci USA*, 104, 6632-6637, 2007; Parker et al., *Protein Eng Des Sel*, 18, 435-444, 2005; Xu et al., *Chemistry & Biology*, 9, 933-942, 2002). Libraries of the FN3 domains have been generated by randomizing also the AB, EF and CD loops (U.S. Pat. Pub. No. 2011/0038866; Int. Pat. Pub. No. WO2011/05133; U.S. Pat. Pub. No. 2011/0124527). Other references for FN3 libraries include Int. Pat. Pub. Nos. WO2002/32925, WO2003/104418, WO2009/023184 and WO2010/060095. Int. Pat. Pub. No. WO2012/016245 describes FN3 domain libraries using CD and FG loops together with surface exposed residues of the beta-sheet.

It would be advantageous to obtain improved fibronectin domain scaffold proteins for both therapeutic and diagnostic purposes. The present disclosure provides such improved proteins.

SUMMARY OF THE INVENTION

One embodiment of the invention is a method of making a library of fibronectin module of type III (FN3) domains having a diversified C-CD-F-FG alternative surface formed by a C beta-strand, a CD loop, an F beta-strand, and an FG loop, comprising providing a reference FN3 domain polypeptide having the amino acid sequence at least 80% identical to that of SEQ ID NO: 27; introducing diversity into the reference FN3 domain polypeptide by mutating at least one C beta-strand residue and at least one F beta-strand residue to form the FN3 domain library having the diversified C-CD-F-FG alternative surface.

A library produced by the methods of the invention.

A method of obtaining a protein scaffold comprising a fibronectin module of type III (FN3) domain having a diversified C-CD-F-FG alternative that specifically binds to a target molecule, comprising contacting or panning the library of claim 11 with the target molecule and isolating a protein scaffold specifically binding to the target molecule with a predefined affinity.

BRIEF DESCRIPTION OF THE DRAWINGS

FIG. 3 shows sequence alignment of the Tencon27 scaffold (SEQ ID NO: 27) and the TCL14 library (SEQ ID NO: 28) having randomized C-CD-F-FG alternative surface. The loop residues are boxed. The particular loop and beta-strand regions are indicated above the sequences.

FIG. 4 shows sequence alignment of the Tencon27 scaffold (SEQ ID NO: 27) and a TCL15 library having randomized A-AB-B-BC-E alternative surface (SEQ ID NO: 61). The loop residues are boxed. The particular loop and beta-strand regions are indicated above the sequences.

FIG. 8 shows sequence alignment of Tencon27 (SEQ ID NO:27), TCL14 (SEQ ID NO: 28), and the designed libraries on FN10 (SEQ ID NO:98), TN3 (SEQ ID NO:99), and Fibcon (SEQ ID NO:62) with randomized C-CD-F-FG alternative surfaces. Residue numbering is based on Tencon27 sequence. The loop residues are boxed. The particular loop and beta-strand regions are indicated above the sequences.

DETAILED DESCRIPTION OF THE INVENTION

Figure 1:
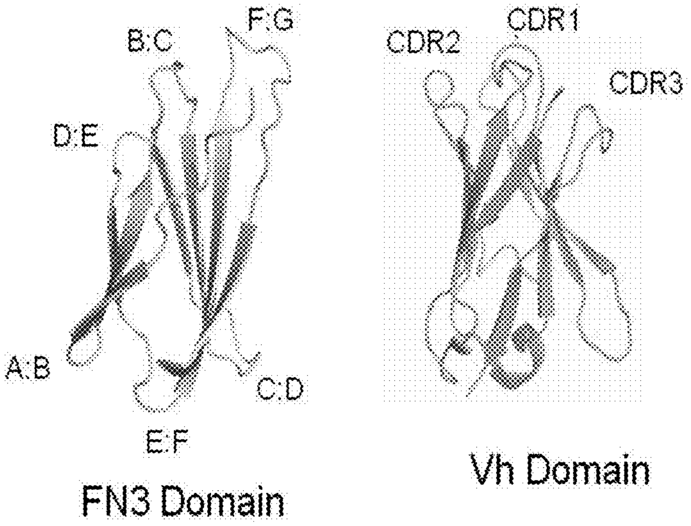
FIG. 1 shows ribbon diagrams of FN3 domain and antibody VH domain structures. Loops of the FN3 domain structurally analogous to CDRs are labeled.

The term "fibronectin module of type III (FN3) domain" as used herein refers to a domain occurring frequently in proteins including fibronectins, tenascin, intracellular cytoskeletal proteins, cytokine receptors and prokaryotic enzymes (Bork and Doolittle, *Proc Nat Acad Sci* USA 89, 8990-8994, 1992; Meinke et al., *J Bacteriol* 175, 1910-1918, 1993; Watanabe et al., *J Biol Chem* 265, 15659-15665, 1990). Exemplary FN3 domains (or modules) are the 15 different FN3 domains present in human tenascin C and the 15 different FN3 domains present in human fibronectin (FN). Individual FN3 domains are referred to by domain number and protein name, e.g., the $3^{rd}$ FN3 domain of tenascin (TN3), or the $10^{th}$ FN3 domain of fibronectin (FN10).

The term "reference FN3 domain" as used herein refers to a wild type or non-naturally occurring FN3 domain that is used as a template into which substitutions are made to generate protein scaffolds specifically binding to a target molecule.

The term "alternative surface" as used herein refers to a surface on a side of the FN3 domain comprising two or more beta strands, and at least one loop. Exemplary alternative surfaces are a C-CD-F-FG surface that is formed by amino acids in the C and the F beta-strands and the CD and the FG loops, and an A-AB-B-BC-E surface that is formed by amino acids in the A, B and E beta-strands and the BC loop.

The term "substituting" or "substituted" or "mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a target molecule with an affinity (Kd) of at least $1\times10^{-6}$ M, and/or bind to a target molecule with an affinity that is at least ten fold greater than its affinity for a nonspecific antigen (for example BSA or casein) as measured by surface plasmon resonance.

The term "target molecule" as used herein refers to a protein, peptide, carbohydrate, lipid, and the like having an antigen or an epitope that is recognized by the FN3 domain of the invention. The target molecule may be naturally or non-naturally occurring.

The term "library" refers to a collection of variants. The library may be composed of polypeptide or polynucleotide variants.

The term "tenascin C" as used herein refers to human tenascin C having a sequence shown in GenBank Acc. No. NP_002151 and in SEQ ID NO: 57. Tenascin C has 15 tandem FN3 domains that have amino acid sequences shown in SEQ ID NOS: 1-15, respectively. The amino acid sequence of the $3^{rd}$ FN3 domain of tenascin C (TN3) is shown in SEQ ID NO: 3.

The term "stability" as used herein refers to the ability of a molecule to maintain a folded state under physiological conditions such that it retains at least one of its normal functional activities, for example, binding to a target molecule.

The present invention provides fibronectin module of type III (FN3) domains that specifically bind to a target molecule, and thus can be widely used in therapeutic and diagnostic applications. The invention is based on a discovery that an alternative surface on a side of the FN3 domain comprising two or more beta-strands and at least one loop can be randomized to generate and select for protein scaffolds specifically binding a target molecule with high affinity. Published FN3-based domain libraries have been generated by diversifying either the top or the bottom loops, areas that structurally resemble CDRs in antibody variable chains, providing curved binding surfaces. In this invention, high affinity binding molecules are selected from FN3 domain libraries displaying concave interaction surfaces generated by randomizing an alternative surface; thus likely increasing the number of epitopes and targets against which high affinity binding protein scaffolds can be selected. The present invention provides polynucleotides encoding the protein domains or complementary nucleic acids thereof, vectors, host cells, and methods of making and using them. The present invention provides methods of making libraries of FN3 domains, and libraries made by methods of the invention.

Fibronectin Type III Domain

Fibronectin Type III (FN3) domain (or module) is a prototypic repeat domain initially identified in fibronectin and now known to be present in various animal protein families including cell surface receptors, extracellular matrix proteins, enzymes, and muscle proteins. Structurally the FN3 domains have a topology very similar to that of immunoglobulin-like domains, except for the lack of disulfide bonds. As is known in the art, naturally occurring FN3 domains have a beta-sandwich structure having seven beta-strands, referred to as A, B, C, D, E, F, and G, linked by six loops, referred to as AB, BC, CD, DE, EF, and FG loops (Bork and Doolittle, *Proc Natl Acad Sci* USA 89, 8990-8992, 1992; U.S. Pat. No. 6,673,901). Three loops, the BC, DE and FG loops are at the top of the FN3 domain, and three, the AB, CD and EF loops at the bottom of the domain (FIG. 1). Table 1 shows several FN3 domain containing proteins, and the number of different FN3 domains associated with each protein. While FN3 domain conformations are highly conserved, the similarity between different domains at the amino acid level is quite low.

FN3 domains may be naturally or non-naturally occurring. Exemplary non-naturally occurring FN3 domains are a consensus FN3 domain designed based on an alignment of select FN3 domains present in a certain protein and incorporating the most conserved (frequent) amino acid at each position to generate the non-naturally occurring FN3 domain. For example, a non-naturally occurring FN3 domain is designed based on a consensus sequence of the 15 FN3 domains from human tenascin C, or based on a consensus sequence of the 15 FN3 domains from human fibronectin. These non-naturally occurring FN3 domains retain the typical topology of the FN3 domains, and can exhibit improved properties such as improved stability when compared to the wild type FN3 domains. Exemplary non-naturally occurring FN3 domains are the Tencon and the Fibcon domains shown in SEQ ID NOS: 16 and 58, respectively, and described in U.S. Pat. Pub. No. 2010/0216708 and U.S. Pat. Pub. No. 2010/0255056.

TABLE 1

| FN3 Protein | Number of FN3 domains |
|---|---|
| Angiopoietin 1 receptor | 3 |
| Contactin protein | 4 |
| Cytokine receptor common β chain | 2 |
| Down syndrome cell adhesion protein | 6 |
| *Drosophila* Sevenless protein | 7 |
| Erythropoietin receptor | 1 |
| Fibronectin | 15 |
| Growth hormone receptor | 1 |
| Insulin receptor | 2 |
| Insulin-like growth factor I receptor | 3 |
| Interferon-γ receptor β chain. | 2 |
| Interleukin-12 β chain | 1 |
| Interleukin-2 receptor β chain | 1 |
| Leptin receptor (LEP-R) | 3 |
| Leukemia inhibitory factor receptor (LIF-R) | 6 |
| Leukocyte common antigen | 2 |
| Neural cell adhesion protein L1 | 4 |
| Prolactin receptor | 2 |
| Tenascin protein | 15 |
| Thrombopoietin receptor. | 2 |
| Tyrosine-protein kinase receptor Tie-1 | 3 |

Amino acid residues defining each loop and each beta-strand are shown for FN3 scaffold Tencon27 (SEQ ID NO: 27) in Table 2. Positions of each loop and beta-strand in tenascin C 3rd FN3 domain (TN3) (SEQ ID NO: 3) and Fibcon (SEQ ID NO: 58) are identical to that of Tencon27. Beta-strand residues can be identified using well known methods, for example, by analysis of 3-dimensional structures generated by x-ray diffraction, nuclear magnetic resonance, or molecular modeling. Where models are not available, analysis of sequence alignments with other known FN3 molecules can be used to predict the boundaries of strand and loop regions. Finally, computer algorithms can be used to predict the presence of beta strands from protein primary sequences.

TABLE 2

| FN3 domain | Tencon27 (SEQ ID NO: 27) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Alternative Surfaces on FN3 Domains

Figure 2A:
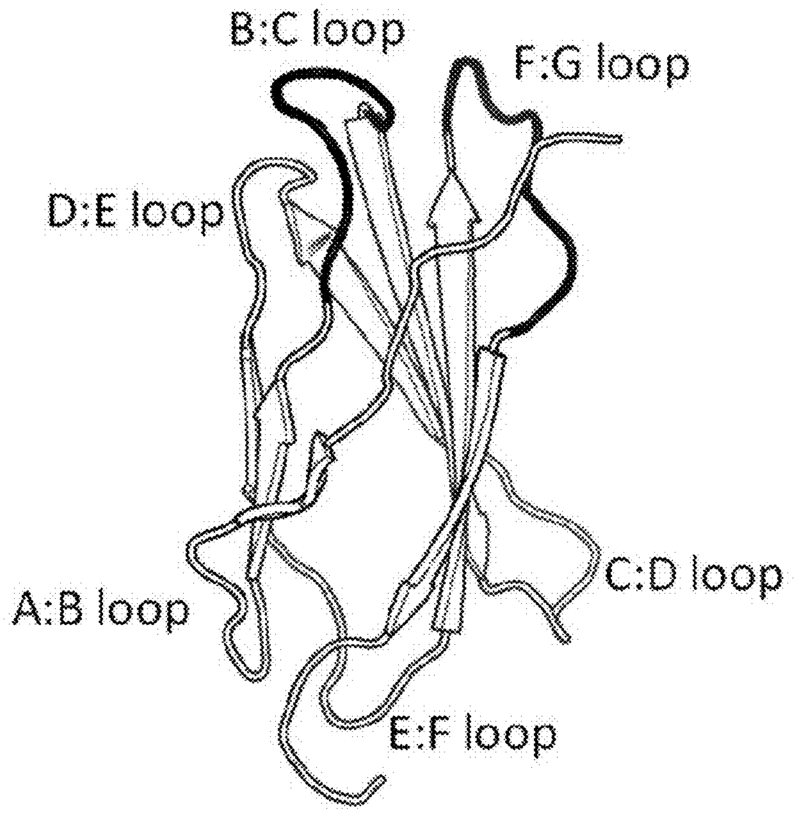
FIGS. 2A-C show structural diagrams that enable comparison between 2A conventional FN3 libraries with randomized loops; 2B FN3 library with randomized C-CD-F-FG alternative surface (TCL14 library); 2C FN3 library with randomized A-AB-B-BC-E surface (TCL15 library). Positions randomized in these library designs are depicted as solid black in the ribbon diagrams.
Figure 2B:
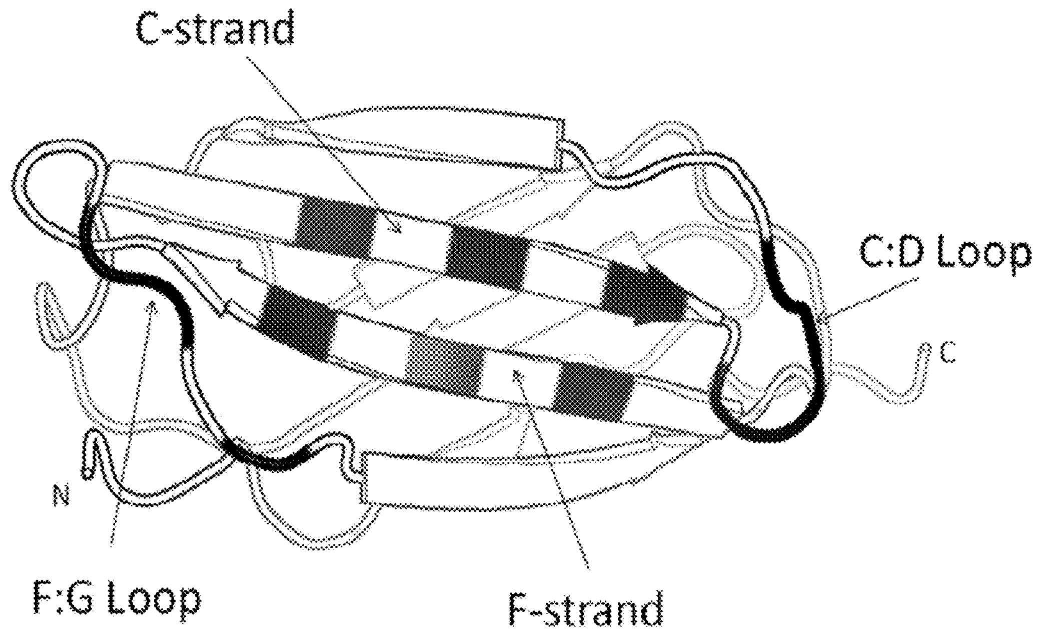
Figure 2C:
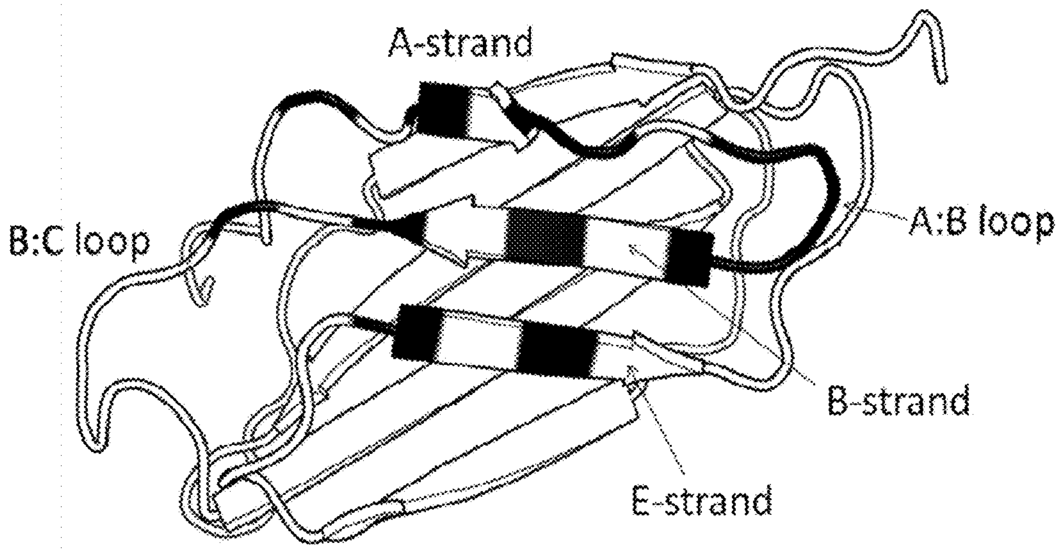

The top (BC, DE, and FG) and the bottom (AB, CD, and EF) loops, e.g., the reported binding surfaces in the FN3 domains are separated by the beta-strands that form the center of the FN3 structure (FIGS. 1, 2A). Alternative surfaces residing on the two "sides" of the FN3 domains having different shapes than the surfaces formed by loops only can be visualized by rotating the FN3 domain structure by 90 degrees (FIGS. 2B, 2C). A slightly concave surface is formed at one side of the FN3 domain by two antiparallel beta-strands, the C and the F beta-strands, and the CD and FG loops, and is herein called the C-CD-F-FG surface. An alternative surface is also formed at the opposite side of the C-CD-F-FG surface by the A, B and E beta-strands and the AB and BC loops, herein called the A-AB-B-BC-E surface.

The alternative surfaces in the FN3 domains are encoded by non-contiguous stretches of amino acid in each FN3 domain. For example, Tencon27 C-CD-F-FG surface is formed by amino acid residues 29-43 and 65-81 of SEQ ID NO: 27, and the Tencon27 A-AB-B-BC-E surface formed by amino acid residues 1-28 and 55-59 of SEQ ID NO: 27, as shown in Table 2.

Protein Scaffolds Based on Randomizing Alternative Surfaces

One embodiment of the invention is an isolated protein scaffold comprising a fibronectin module of type III (FN3) domain comprising an alternative surface, wherein the alternative surface has at least one amino acid substitution in each beta-strand and each loop forming the alternative surface when compared to a reference FN3 domain.

In another embodiment, the protein scaffold of the invention specifically binds to a target molecule not specifically bound by the reference FN3 domain.

In another embodiment, the reference FN3 domain comprises a SEQ ID NO: 27.

In another embodiment, the protein scaffold of the invention comprises a C-CD-F-FG alternative surface formed by a C beta-strand, a CD loop, an F beta-strand, and a FG loop.

In another embodiment, the C beta-strand, the CD loop, the F beta-strand, or the FG loop forming the C-CD-F-FG alternative surface comprise certain amino acid sequences as shown in Tables 4 and 5 and in SEQ ID NOS: 45-48.

In another embodiment, the C beta-strand comprises an amino acid sequence DSFLIQYQE (SEQ ID NO: 33) having substitutions at 1, 2, 3, or 4 residues, the F beta-strand comprises an amino acid sequence TEYTVSIYGV (SEQ ID NO: 39) having substitutions at 1, 2, 3, 4, or 5 residues, the C beta-strand and the CD loop comprises an amino acid sequence DSFLIQYQESEKVGE (SEQ ID NO: 42) having substitutions at 1, 2, 3, 4, 5, 6, 7, 8, 9, or 10 residues, or the F beta-strand and the FG loop comprises and amino acid sequence TEYTVSIYGVKGGHRSN (SEQ ID NO: 43) having substitutions at 1, 2, 3, 4, 5, 6, 7, 8, 9, 10, or 11 residues.

In another embodiment, the C beta-strand and the F beta-strand comprise an amino acid sequence at least 67% identical to SEQ ID NO:33 and at least 70% identical to SEQ ID NO:39, respectively, the C beta-strand and the CD loop comprises an amino acid sequence at least 53% identical to SEQ ID NO: 42, or the F beta-strand and the FG loop comprises an amino acid sequence at least 65% identical to SEQ ID NO: 43.

In another embodiment, the protein scaffold of the invention comprises a FN3 domain comprising an amino acid sequence shown in SEQ ID NO: 28.

In another embodiment, the protein scaffold of the invention comprises a fibronectin module of type III (FN3) domain comprising:

an A beta-strand, an AB loop, a B beta-strand, a BC loop, a D beta-strand, a DE loop, an E beta-strand, an EF loop and a G beta-strand having amino acid sequences identical to SEQ ID NO: 27 at residues 1-12, 13-16, 17-21, 22-28, 44-50, 51-54, 55-59, 60-64, and 82-89, respectively;

- a C beta-strand and a CD loop having an amino acid sequence at least 53% identical to SEQ ID NO: 42; and
- a F beta-strand and an FG loop having an amino acid sequence at least 65% identical to SEQ ID NO: 43, optionally having at least one substitution at amino acid positions corresponding to amino acid residues 11, 14, 17, 37, 46, 73, or 86 of SEQ ID NO: 27, wherein the protein scaffold specifically binds to a target molecule not specifically bound by a reference FN3 domain.

In another embodiment, the protein scaffold of the invention comprises a FN3 domain comprising an amino acid sequence at least 80%, 85%, 90%, 91%, 92%, 93%, 94%, 95%, 96%, 97%, 98%, 99%, or 100% identical to the amino acid sequences shown in SEQ ID NO: 27.

In another embodiment, the protein scaffold of the invention comprises an A-AB-B-BC-E alternative surface formed by an A beta-strand, an AB loop, a B beta-strand, a BC loop, and an E beta-strand.

In another embodiment, the A beta-strand, the AB loop, the B beta-strand, and the BC loop forming the A-AB-B-BC-E alternative surface comprise certain amino acid sequences as shown in Tables 4 and 5 and in SEQ ID NOS: 49-50.

In another embodiment, the A beta-strand, the AB loop, the B beta-strand and the BC loop comprise an amino acid sequence that is at least 59% identical to SEQ ID NO:44, and the E beta-strand comprises an amino acid sequence that is at least 60% identical to SEQ ID NO: 37.

In another embodiment, the protein scaffold of the invention comprises an FN3 domain comprising an amino acid sequence shown in SEQ ID NO: 61.

In another embodiment, an isolated protein scaffold of the invention comprises a fibronectin module of type III (FN3) domain comprising a fibronectin module of type III (FN3) domain comprising:

- a C beta-strand, a CD loop, a D beta-strand, a DE loop, an EF loop, an F beta-strand, an FG loop, and a G beta-strand having amino acid sequences identical to SEQ ID NO: 27 at residues 29-37, 38-43, 44-50, 51-54, 60-64, 65-74, 75-81, and 82-89, respectively;
- an A beta-strand, an AB loop, a B beta-strand, and a BC loop having an amino acid sequence that is at least 59% identical to SEQ ID NO: 44; and
- an E beta-strand having an amino acid sequence that is at least 60% identical to SEQ ID NO: 37, optionally having at least one substitution at amino acid positions corresponding to amino acid residues 11, 14, 17, 37, 46, 73, or 86 of SEQ ID NO: 27, wherein the protein scaffold specifically binds to a target molecule not specifically bound by a reference FN3 domain.

The FN3 domains specifically binding to a target molecule can be generated by randomizing a subset of the residues that form the alternative surface. For example, at least one, two, three, four, five, six, seven, eight, nine, or ten residues can be randomized in each beta-strand and each loop contributing to the alternative surface. Additional residues can be randomized to increase diversity of the library. For example, 20%, 30%, 40%, 50%, 60%, 70%, 75%, 80%, 85%, 90%, or 95% of the residues in each beta-strand and each loop forming the alternative surface may be randomized. Alternatively, FN3 domains specifically binding to a target molecule can be generated by randomizing a subset of the residues in the beta-strands contributing to the alternative surface, without randomizing any of the loops. For example, at least one, two, three, four, five, six, seven, eight, nine, or ten residues in each strand contributing to the alternative surface can be randomized. Library diversity can be increased by randomizing additional residues residing in the beta-strands. For example, 20%, 30%, 40%, 50%, 60%, 70%, 75%, 80%, 85%, 90%, or 95%, of the residues in each beta-strand forming the alternative surface may be randomized.

Beta-strands have a repeating structure with the side-chain of every other residue exposed to the surface of the protein. Surface exposed side-chains are determined by examination of three dimensional structures or by comparison to sequences of FN3 domains with known structure by multiple sequence alignment. All or a subset of surface exposed residues in the beta-strands contributing to the alternative surface may be chosen to be randomized. For example, Tencon27 (SEQ ID NO: 27) C-CD-F-FG alternative surface has four surface exposed residues in the C beta-strand (S30, L32, Q34, and Q36) and five surface exposed residues in the F beta-strand (E66, T68, S70, Y72, and V74), residue numbering based on SEQ ID NO: 27. One or more of these residues may be randomized to generate a library. Residues at the junction of the alternative surface, such as S30, E66 and V74 may or may not be randomized. Randomization of the buried residues of the beta-strands may result in the destabilization of the scaffold due to the loss of hydrophobic contacts in the core of the structure. The buried residues may be randomized so that only a subset of amino acids is used, for example only hydrophobic amino acids.

A subset or all residues in the loop regions contributing to the alternative surface may be randomized. For example, 0, 1, 2, 3, 4, 5, 6, 7, 8, 9, 10, 11, 12, or 13 positions may be substituted in the CD and/or FG loops contributing to the alternative surface. Glycine residues in the loops, such as G42, G76 and/or G77 in Tencon27, can provide flexibility and may or may not be randomized. Residues at the beta-strand/loop boundaries, such as E43 in Tencon27 may or may not be randomized. Additional residues in the beta-strand or loop regions may be included or excluded from randomization. For example, residues that appear to be required for stabilization identified based on, for example, analysis of crystal structures of the FN3 domains, may or may not be randomized. For example, S80 in Tencon27 makes contacts with the FN3 domain core to potentially stabilize the FG loop, and K75 partially faces away from the alternative surface. Thus, both these residues may be excluded from initial library design. In an exemplary FN3 domain library having randomized C-CD-F-FG surface, residues that can be randomized include residues at positions 30, 32, 34, 36, 38, 39, 40, 41, 42, 43, 66, 68, 70, 72, 74, 75, 76, 77, 78, 79, 80, or 81 of SEQ ID NO: 27. In an exemplary FN3 domain library having randomized A-AB-B-BC-E surface, residues that can be randomized include residues at positions 6, 8, 10, 11, 12, 13, 14, 15, 16, 18, 20, 22, 23, 24, 25, 26, 27, 55, and 57.

Diversity at loops contributing to alternative surfaces may be achieved by insertion and/or deletions of residues at loops. For example, the FG and/or CD loops may be extended by 1-22 amino acids, or decreased by 1-3 amino acids. The FG loop in Tencon27 is 7 amino acids long, whereas the corresponding loop in antibody heavy chains ranges from 4-28 residues. To provide maximum diversity, the loops contributing to alternative surfaces, for example, the FG loop, may be diversified in sequence as well as in length to correspond to the antibody CDR3 length range of 4-28 residues.

The resulting FN3 domains specifically binding to a target molecule can be further modified at residues residing outside of or within the alternative surface for the purpose of for example improving stability, reducing immunogenicity, enhancing binding affinity, on-rate, off-rate, half life, solubility, or any other suitable characteristics. In one way to achieve this goal, the scaffold proteins can be optionally prepared by a process of analysis of the parental sequences and various conceptual engineered products using three-dimensional models of the parental and engineered sequences. Three-dimensional models are commonly available and are familiar to those skilled in the art. Computer programs are available which illustrate and display probable three-dimensional conformational structures of selected candidate sequences and can measure possible immunogenicity (e.g., Immunofilter program of Xencor, Inc. of Monrovia, Calif.). Inspection of these displays permits analysis of the likely role of the residues in the functioning of the candidate sequence, for example, residues that influence stability of the scaffold protein or the ability of the candidate scaffold protein to bind its target molecule. In this way, residues can be selected and combined from the parent and reference sequences so that the desired characteristics, such as improved scaffold stability is achieved. Alternatively, or in addition to the above procedures, other suitable methods of engineering can be used as known in the art.

Desirable physical properties of FN3 domains of the invention include high thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, *Curr Opin Biotechnol*, 12, 371-375, 2001). High thermal stability may increase the yield of the expressed protein, improve solubility or activity, decrease immunogenicity, and minimize the need of a cold chain in manufacturing.

Residues that can be substituted to improve any characteristics of the FN3 domains of the invention can be determined by making the substitution and assaying for the desired characteristics of the scaffold. Exemplary FN3 domain-based scaffold with improved characteristics are the Tencon scaffold (SEQ ID NO: 16) or the Tencon27 scaffold (SEQ ID NO: 27) that is modified at one or more amino acid residue positions 11, 14, 17, 37, 46, 73, or 86.

In terms of loss of stability, i.e., "denaturing" or "denaturation" of a protein, is meant the process where some or all of the three-dimensional conformation imparting the functional properties of the protein has been lost with an attendant loss of activity and/or solubility. Forces disrupted during denaturation include intramolecular bonds, for example, electrostatic, hydrophobic, Van der Waals forces, hydrogen bonds, and disulfides. Protein denaturation can be caused by forces applied to the protein or a solution comprising the protein, such as mechanical force (for example, compressive or shear-force), thermal, osmotic stress, change in pH, electrical or magnetic fields, ionizing radiation, ultraviolet radiation and dehydration, and by chemical denaturants.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("TM") temperature, the temperature in ° Celsius (° C.) at which ½ of the molecules become unfolded, using standard methods. Typically, the higher the TM, the more stable the molecule. In addition to heat, the chemical environment also changes the ability of the protein to maintain a particular three dimensional structure.

In one embodiment, the FN3 domains of the invention exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the TM.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

In one embodiment, the scaffolds of the invention exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same scaffold prior to engineering measured by using guanidinium hydrochloride as a chemical denaturant. Increased stability can be measured as a function of decreased tryptophan fluorescence upon treatment with increasing concentrations of guanidine hydrochloride using well known methods.

The FN3 domains specifically binding to a target molecule of the invention can be generated using any FN3 domain as a template for substitutions according to methods provided within. Exemplary FN3 domains having randomized alternative surfaces are the 3rd FN3 domain of tenascin C (TN3) (SEQ ID NO: 3), Tencon (SEQ ID NO: 16), Tencon27 (SEQ ID NO: 27), Fibcon (SEQ ID NO: 58), and the $10^{th}$ FN3 domain of fibronectin (FN10) (SEQ ID NO: 97). The amino acid positions delineating the alternative surfaces in Tencon27 are shown in Table 2 and FIG. 8, and are identical in Tencon, TN3, and Fibcon linear sequence. The amino acid positions delineating the alternative surface in FN10 is shown in FIG. 8. The residues forming the alternative surfaces in other FN3 domains can be identified by examination of three dimensional structures where available or by analysis of sequence alignments of FN3 domains by well known methods.

The FN3 domains of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng*. 8, 725-731, 1995; Robinson & Sauer, *Biochemistry* 35, 109-116, 1996; U.S. Pat. No. 5,856,456).

The FN3 domains of the present invention may be used as bispecific molecules wherein the first alternative surface in a domain has specificity for a first target molecule and the second alternative surface in the same domain has specificity for a second target molecule. An exemplary bispecific protein domain is a variant of Tencon27 which binds a first target molecule at the C-CD-F-FG surface, and a second target molecule at the A-AB-B-BC-E surface.

The FN3 domains of the present invention may incorporate other subunits for example via covalent interaction. All or a portion of an antibody constant region may be attached to the FN3 domain to impart antibody-like properties, especially those properties associated with the Fc region, e.g., complement activity, half-life, etc. For example, Fc effector functions such as Clq binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), etc. can be provided and/or controlled by modifying residues in the Fc responsible for these activities (for review; see Strohl, *Curr Opin Biotechnol*. 20, 685-691, 2009).

Additional moieties may be incorporated into the FN3 domains of the invention such as toxin conjugates, albumin or albumin binders, polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced FN3 domains of the invention.

FN3 domains incorporating additional moieties may be compared for functionality by several well known assays. For example, altered FN3 domain properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating protein scaffold pharmacokinetic properties in in vivo models.

Generation and Production of FN3 Domain Proteins

One embodiment of the invention is a method of making a library of fibronectin module of type III (FN3) domains comprising an alternative surface, wherein the alternative surface has at least one amino acid substitution when compared to a reference FN3 domain, comprising: providing a polynucleotide encoding a reference FN3 domain; generating a library of polynucleotide sequences of the reference FN3 domain by randomizing the alternative surface; translating the library in vitro or expressing the library in a host.

Another embodiment of the invention is a method of making a library of fibronectin module of type III (FN3) domains having a diversified C-CD-F-FG alternative surface formed by a C beta-strand, a CD loop, an F beta-strand, and an FG loop, comprising providing a reference FN3 domain polypeptide having the amino acid sequence at least 80% identical to that of SEQ ID NO: 27; introducing diversity into the reference FN3 domain polypeptide by mutating at least one C beta-strand residue and at least one F beta-strand residue to form the FN3 domain library having the diversified C-CD-F-FG alternative surface.

In the methods of making the library of the invention, 1, 2, 3 or 4 residues in the C beta-strand can be mutated with the proviso that S30 is not mutated (residue numbering according to SEQ ID NO: 27).

In the methods of making the library of the invention, the C beta-strand residues L32, Q34 and Q36 can be mutated (residue numbering according to SEQ ID NO: 27).

In the methods of making the library of the invention, 1, 2, 3 or 4 residues in the F beta-strand can be mutated with the proviso that E66 is not mutated (residue numbering according to SEQ ID NO: 27).

In the methods of making the library of the invention, the F-beta strand residues T68, S70 and Y72 can be mutated (residue numbering according to SEQ ID NO: 27).

In the methods of making the library of the invention, 1, 2, 3 or 4 residues in the CD loop residues can be mutated with the proviso that G42 and E43 are not mutated (residues numbering according to SEQ ID NO: 27).

In the methods of making the library of the invention, the residues S38, E39, K40 and V41 in the CD loop can be mutated.

In the methods of making the library of the invention, 1, 2, 3 or 4 residues in the FG loop can be mutated with the proviso that the residues K75, G76, G77 and S80 are not mutated (residue numbering according to SEQ ID NO: 27).

In the methods of making the library of the invention, the residues H78, R79 and N81 in the FG loop can be mutated (residue numbering according to SEQ ID NO: 27).

In the methods of making the library of the invention, the reference FN3 domain comprises an amino acid sequence of SEQ ID NO: 27, optionally comprising at least one substitution at amino acid positions 11, 14, 17, 37, 46, 73, or 86.

Other reference FN3 domains may be used in the methods of the invention, such as Tencon (SEQ ID NO: 16) or variants thereof as shown in SEQ ID NOS: 17-26 and in Table 3.

Another embodiment of the invention is a library produced by the methods of the invention.

Generation of the scaffold proteins, FN3 domains (or modules) of the invention, is typically achieved at the nucleic acid level. The libraries of the FN3 domains of the invention having substituted codons at one or more specific residues can be synthesized for example using standard PCR cloning methods, or chemical gene synthesis according to methods described in U.S. Pat. Nos. 6,521,427 and 6,670,127. Codons can be randomized using well known methods, for example degenerate oligonucleotides matching the designed diversity, or using Kunkel mutagenesis Kunkel et al., *Methods Enzymol*. 154, 367-382, 1987).

Libraries can be randomized at chosen codons using a random or defined set of amino acids. For example, variants in the library having random substitutions can be generated using NNK codons, which encode all 20 naturally occurring amino acids. In other diversification schemes, DVK codons can be used to encode amino acids Ala, Trp, Tyr, Lys, Thr, Asn, Lys, Ser, Arg, Asp, Glu, Gly, and Cys. Alternatively, NNS codons can be used to give rise to all 20 amino acid residues and simultaneously reducing the frequency of stop codons. The codon designations are according to the well known IUB code.

The FN3 domains of the invention as any other proteins are prone to a variety of physical and/or chemical instabilities, resulting in adverse effects on the downstream processing. For instance, physical and chemical instability may lead to aggregation, degradation, reduced product yield, loss of potency, increased potential for immunogenicity, molecular heterogeneity, and loss of activity. Thus, presence of possible instability-inducing residues and recognition sequences may be minimize during the design of the libraries. For example, surface exposed methionine and tryptophan may be oxidized in storage conditions, possibly leading to loss in the protein scaffold potency. Presence of asparagine, in addition to contributing to well known N-glycosylation recognition sites (NXS/T) may be deamidated when followed by glycine, possibly generating heterogeneicity (Robinson, *Proc Natl Acad Sci USA*, 99, 5283-5288, 2002). Some or all of these amino acids thus may or may not be omitted from the mix used to randomize selected position. Furthermore, cysteine and proline may be omitted to minimize disulphide bridge formation and disruption of beta sheets.

Libraries of FN3 domains with biased amino acid distribution at positions to be diversified can be synthesized for example using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule.

Synthesis of oligonucleotides with selected nucleotide "degeneracy" at certain positions is well known in that art, for example the TRIM approach (Knappek et al., *J Mol Biol* 296, 57-86, 1999; Garrard & Henner, *Gene* 128,103-109, 1993). Such sets of nucleotides having certain codon sets can be synthesized using commercially available nucleotide or nucleoside reagents and apparatus.

In an exemplary diversification scheme, Tencon27 FN3 domain (SEQ ID NO: 27) residues L32, Q34 and Q36 in the C beta-strand, S38, E39, K40 and V41 in the CD loop, T68, S70 and Y72 in the F beta-strand, and H78, R79, and N81 in the FG loop are randomized with NNS codons.

Standard cloning and expression techniques are used to clone the libraries into a vector or synthesize double stranded cDNA cassettes of the library, to express, or to translate the libraries in vitro. For example, cis-display can be used to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., *Proc Natl Acad Sci* USA 101, 2806-2810, 2004). Other methods can be used, for example ribosome display (Hanes and Pluckthun, *Proc Natl Acad Sci USA*, 94, 4937-4942, 1997), mRNA display (Roberts and Szostak, *Proc Natl Acad Sci USA*, 94, 12297-12302, 1997), or other cell-free systems (U.S. Pat. No. 5,643,768). The libraries of protein scaffolds may be expressed as fusion proteins displayed on the surface for example of any suitable bacteriophage. Methods for displaying fusion polypeptides on the surface of a bacteriophage are well known (U.S. Pat. Pub. No. 2011/0118144; Int. Pat. Pub. No. WO2009/085462; U.S. Pat. Nos. 6,969,108; 6,172,197; 5,223,409; 6,582,915; 6,472,147).

Screening

Screening engineered protein FN3 domains or libraries of FN3 domain variants for specific binding to target molecules can be achieved for example by producing the library using cis display as described in Examples and in Odegrip et al., *Proc Natl Acad Sci USA* 101, 2806-2810, 2004, and assaying the library for specific binding to a target molecule by any method known in the art. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York).

The FN3 domains of the invention can bind human or other mammalian proteins with a wide range of affinities ($K_D$). Typically a FN3 domain of the present invention can bind to a target protein with a $K_D$ equal to or less than about $10^{-7}$ M, $10^{-8}$ M, $10^{-9}$ M, $10^{-10}$ M, $10^{-11}$ M, $10^{-12}$ M, $10^{-13}$ M, $10^{-14}$ M, or $10^{-15}$ M as determined by surface plasmon resonance or the Kinexa method, as practiced by those of skill in the art. The affinity of a FN3 domain for an antigen can be determined experimentally using any suitable method. (See, for example, Berzofsky, et al., "Antibody-Antigen Interactions," In *Fundamental Immunology*, Paul, W. E., Ed., Raven Press: New York, N.Y. (1984); Kuby, Janis *Immunology*, W. H. Freeman and Company: New York, N.Y. (1992); and methods described herein). The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are preferably made with standardized solutions of protein scaffold and antigen, and a standardized buffer, such as the buffer described herein.

Nucleic Acid Molecules and Vectors

The invention provides for nucleic acids encoding the FN3 domains of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the protein scaffolds and libraries of the protein scaffolds of the invention are also within the scope of the invention.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

An exemplary polynucleotide comprises sequences for a Tac promoter, sequences encoding the FN3 domain library and repA, cis element, and a bacterial origin of replication (ori). Another exemplary polynucleotide comprises a pelB or ompA signal sequence, pIII or pIX bacteriophage coat protein, FN3 domain, and a polyA site. Exemplary polynucleotides encoding the TCL14 library and Tencon27 are shown in SEQ ID NOs: 100 and 101, respectively.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Host Cell Selection or Host Cell Engineering

A FN3 domain of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The host cell chosen for expression may be of mammalian origin or may be selected from COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD(DE3), XL1-Blue, JM109, HMS174, HMS174 (DE3), and any of the natural or engineered *E. coli* spp, *Klebsiella* spp., or *Pseudomonas* spp strains.

Uses of FN3 Domains of the Invention

The compositions of the FN3 domain (module)-based molecules described herein and generated by any of the above described methods may be used to diagnose, monitor, modulate, treat, alleviate, help prevent the incidence of, or reduce the symptoms of human disease or specific pathologies in cells, tissues, organs, fluid, or, generally, a host. A FN3 domain engineered for a specific purpose may be used to treat an immune-mediated or immune-deficiency disease, a metabolic disease, a cardiovascular disorder or disease; a malignant disease; a neurologic disorder or disease; an infection such as a bacterial, viral or parasitic infection; or other known or specified related condition including swelling, pain, and tissue necrosis or fibrosis.

Such a method can comprise administering an effective amount of a composition or a pharmaceutical composition comprising at least one FN3 domain specifically binding a target molecule to a cell, tissue, organ, animal or patient in need of such modulation, treatment, alleviation, prevention, or reduction in symptoms, effects or mechanisms. The effective amount can comprise an amount of about 0.001 to 500 mg/kg per single (e.g., bolus), multiple or continuous administration, or to achieve a serum concentration of 0.01-5000 μg/ml serum concentration per single, multiple, or continuous administration, or any effective range or value therein, as done and determined using known methods, as described herein or known in the relevant arts.

Pharmaceutical Compositions Comprising FN3 Domain-Based Proteins

The FN3 domains specifically binding target molecules which are modified or unmodified, monomers, dimers, or multimers, mono-, bi- or multi-specific, can be isolated using separation procedures well known in the art for capture, immobilization, partitioning, or sedimentation, and purified to the extent necessary for commercial applicability.

For therapeutic use, the FN3 domains specifically binding a target molecule may be prepared as pharmaceutical compositions containing an effective amount of the FN3 domain as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the agent of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the FN3 domains specifically binding a target molecule may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

While having described the invention in general terms, the embodiments of the invention will be further disclosed in the following examples that should not be construed as limiting the scope of the claims.

EXAMPLE 1

Tencon Scaffold

Tencon Design

The third fibronectin module of type III (Fn3) domain from human tenascin C (SEQ ID NO: 3) can be used as a protein scaffold that can be engineered to bind to specific target molecules. The melting temperature of this domain is 54° C. in PBS in its native form.

In order to produce a protein scaffold with a similar structure and improved physical properties, such as an improved thermal stability, a consensus sequence was designed based on an alignment of 15 FN3 domains from human tenascin C (shown in SEQ ID NOS: 1-15). The 15 selected FN3 domains have sequence identities to each other ranging from 13 to 80%, with an average sequence identity among pairs of 29%. A consensus sequence designated as Tencon (SEQ ID NO: 16) was designed by incorporating the most conserved (frequent) amino acid at each position (see U.S. Pat. Pub. No. 2010/0216708). In pairwise alignments, Tencon is identical to the FN3 domains from tenascin C at 34-59% of positions with an average sequence identity of 43%.

Tencon Expression and Purification

The amino acid sequence of Tencon was back translated, resulting in the cDNA sequence shown in SEQ ID NO: 59. The cDNA was amplified and cloned into modified pET15 vector using routine methods. The protein was expressed as a C-terminal $His_6$-fusion protein in soluble form in *E. coli*, and purified using standard Ni-NTA agarose using elution in 500 mM imidazole. The desired fractions were pooled and dialyzed into PBS pH 7.4. As a second purification step the protein was loaded onto a Superdex-75 HiLoad 16/60 column (GE Healthcare) equilibrated in PBS. The fractions containing Tencon were pooled and concentrated using a Centriprep UltraCel YM-3 concentrator (Amicon). SDS-PAGE analysis showed that Tencon migrates between 6 and 14 kDa, in agreement with the expected mass of 10.7 kDa for the monomeric protein. A yield of >50 mg of pure Tencon protein per liter of culture was obtained.

Tencon Biophysical Characterization

The structure and stability of Tencon was characterized by circular dichroism spectroscopy (CD) and differential scanning calorimetry (DSC). CD measurements were made on an AVIV spectrometer at 20° C. in PBS and a concentration of 0.2 mg/mL. The spectrum showed a minimum at 218 nm, suggestive of beta-sheet structure as expected for a protein belonging to the FN3 family. DSC data was obtained by heating 0.5 mg/mL solutions of the $3^{rd}$ FN3 domain from tenascin C (TN3) or Tencon in PBS from 35° C. to 95° C. at a rate of 1° C./minute in an N-DSCII calorimeter (Applied Thermodynamics). From this data, melting temperatures of 54° C. and 78° C. were calculated for TN3 and Tencon, respectively, using CpCalc (Applied Thermodynamics) software. The folding and unfolding of both domains is reversible at these temperatures. Thus, the generated Tencon scaffold demonstrates an improved thermal stability when compared to that of the TN3. Based on this stability increase, the Tencon scaffold is likely to be more amenable to amino acid substitution and easier to manufacture. Mutations that decrease protein stability are likely to be better tolerated in the context of a more stable scaffold and thus a scaffold with enhanced stability is likely to yield more functional, well folded binders from a library of scaffold variants.

Tencon Display on M13 Phage

The cDNA (SEQ ID NO: 59) encoding the Tencon amino acid sequence was subcloned into the phagemid expression vector pPep9 (Int. Pat. Pub. No. WO2008/079973) by standard PCR and restriction digest cloning, resulting in the vector pTencon-pIX. This vector expresses N-terminally Myc-tagged Tencon as a C-terminal fusion to the N-terminus of the bacteriophage M13 pIX protein under Lac promoter (allowing for lower levels of expression without IPTG and increased expression after the addition of IPTG) utilizing the OmpA signal sequence. A short TSGGGGS linker (SEQ ID NO: 60) was inserted between Tencon and pIX to prevent steric interactions between these proteins.

For confirmation of display on the surface of the M13 phage particle, single colony transformants of pTencon-pIX in XL1-Blue *E. coli* were grown at 37° C. until reaching mid-log phase and rescued with $6^{10}$ pfu of VCSM13 helper phage. Supernatants were collected from the rescued cultures after 16 hour expansion in 2YT media supplemented with ampicillin followed by 1 mM IPTG induction, centrifuged at 4000×g for 20 minutes and stored at 4° C. for analysis.

Binding of the phage particles to an anti-Myc antibody (Life Technologies, Carlsbad, Calif.) was used to confirm the display of the Myc-Tencon construct on the M13 phage surface. A Maxisorp plate was coated overnight at a concentration of 2.5 μg/mL with anti-Myc or an anti-av antibody (negative control) and blocked with SuperBlock T20 (Thermo Scientific, Rockford Ill.). Two-fold serial dilutions of the phagemid culture supernatant described above were made in PBS and added to the wells of the coated plate. After 1 hour, the plate was washed with TBST and an anti-M13 HRP antibody was added to each well and washed with TBST following a 1-hour incubation. The Roche BD ELISA POD substrate was added and luminescence detected on a Tecan plate reader

EXAMPLE 2

Stabilizing Mutations in Tencon

Tencon libraries, FG7 and BC6/FG7, designed to introduce diversity into the FG and FG and BC loops simultaneously have been described (U.S. Pat. Pub. No. 2010/0255056; U.S. Pat. Pub. No. 2010/0216708).

Design of Variants

Mutants were designed to improve the folding stability of Tencon (SEQ ID NO: 16). Several point mutations were made to produce substitution of individual residues of SEQ ID NO: 16, such as N46V (Tencon17; SEQ ID NO:17), E14P (Tencon18; SEQ ID NO:18), E11N (Tencon19; SEQ ID NO:19), E37P (Tencon20; SEQ ID NO:20), and G73Y (Tencon21; SEQ ID NO:21) which were predicted to improve the scaffold stability by the program PoPMuSiC v2.0 (Dehouck et al., *Bioinformatics*, 25, 2537-2543, 2009). The mutant E86I (Tencon22; SEQ ID NO:22) had been previously found to stabilize a homologous protein, the $3^{rd}$ FN3 domain from human tenascin C (WO2009/086116). The L17A mutation (Tencon26; SEQ ID NO: 26) was found to significantly stabilize Tencon during alanine scanning experiments in which all loop residues of Tencon were replaced with alanine independently (data not shown). Following an initial round of stability assays, the combinatorial mutants N46V/E86I (Tencon23; SEQ ID NO:23), E14P/N46V/E86I (Tencon24; SEQ ID NO:24), and L17A/N46V/E86I (Tencon25; SEQ ID NO:25) were produced to further increase stability.

Expression and Purification

Mutations in the Tencon coding sequence were made using a QuikChange mutagenesis kit (Stratagene), and the mutant proteins were expressed and purified using standard protocols as $HIS_6$ fusion proteins. The proteins were eluted from Ni-NTA (Novagen) columns in 50 mM sodium phosphate pH 7.4, 500 mM NaCl, and 250 mM imidazole. After elution, the proteins were dialyzed into PBS pH 7.4.

Characterization of Thermal Stability

The thermal stabilities of Tencon and each mutant protein in pBS pH 7.4 (2-3 mg/mL) were measured by capillary differential scanning calorimetry (DSC). Melting temperatures were measured for these samples using a VP-DSC instrument equipped with an autosampler (MicroCal, LLC). Samples were heated from 10° C. to 95° C. or 100° C. at a rate of 1° C. per minute. A buffer only scan was completed between each sample scan in order to calculate a baseline for integration. Data were fit to a two state unfolding model following subtraction of the buffer only signal. Reversibility of thermal denaturation was determined by repeating the scan for each sample without removing it from the cell. Reversibility was calculated by comparing the area under the curve from the $1^{st}$ scan with the $2^{nd}$ scan. Results of the DSC experiments are presented in Table 3 as the values derived from complete melting curves (Tm(Kcal)). Single mutants Tencon17, Tencon18, Tencon19, and Tencon22 had improved thermal stability compared to the parent Tencon sequence. Only Tencon21 was significantly destabilizing. Combinatorial mutants Tencon23, Tencon24, and Tencon25 and all had a significantly larger enhancement of the stability, indicating that the designed mutations are additive with respect to improving thermal stability.

Denaturation by Guanidine Hydrochloride

The abilities of Tencon and each mutant to remain folded upon treatment with increasing concentrations of guanidine hydrochloride (GdmCl) as measured by tryptophan fluorescence were used to assess stability. Tencon contains only one tryptophan residue. The tryptophan residue is buried within the hydrophobic core and thus fluorescence emission at 360 nm is a sensitive measure of the folded state of this protein. 200 μL of a solution containing 50 mM sodium phosphate pH 7.0, 150 mM NaCl, and variable concentrations of GdmCl from 0.48 to 6.63 M were pipetted into black, non-binding, 96-well plates (Greiner) in order to produce a 17 point titration. 10 μL of a solution containing the Tencon mutants were added to each well across the plate to make a final protein concentration of 23 μM and mixed by pipetting up and down gently. After incubation at room temperature for 24 hours, fluorescence was read using a Spectramax M5 plate reader (Molecular Devices, Sunnyvale, Calif.) with excitation at 280 nm and emission at 360 nm. Fluorescence signal was converted to fraction unfolded using the equation (Pace, *Methods Enzymol* 131:266-280, 1986):

$$f_u=(y_F-y)/(y_F-y_u)$$

Where $y_F$ is the fluorescence signal of the folded sample and $y_u$ of the unfolded sample. The mid-points of the unfolding transition and slope of the transition were determined by fitting to the equation below (Clarke et al., 1997):

$$F=\frac{(\alpha_N+\beta_N[D])+(\alpha_D+\beta_D[D])\exp(m([D]-[D]_{50\%})/RT)}{1+\exp(m([D]-[D]_{50\%})/RT)}$$

Where F is the fluorescence at the given denaturant concentration, $\alpha_N$ and $\alpha_D$ are the y-intercepts of the native and denatured state, $\beta_X$ and $\beta_D$ are the slopes of the baselines for the native and denatured state, [D] is the concentration of GdmCl, $[D]_{30\%}$ the GdmCl concentration at which point 50% of the sample is denatured, m the slope of the transition, R the gas constant, and T the temperature. The free energy of folding for each sample was estimated using the equation (Pace 1986 supra; Clarke et al., *J Mol Biol* 270, 771-778, 1997): $\Delta G=m[D]_{30\%}$.

It is often difficult to accurately measure the slope of the transition, m, for such curves. Additionally, the mutations described here are not expected to alter the folding mechanism of tencon. Thus, the m value for each mutant was measured and the values averaged (Pace 1986 supra) to produce an m=3544 cal/mol/M used for all free energy calculations. The results of these calculations are presented in Table 3. The results for GdmCl unfolding experiments demonstrate that the same mutants that stabilize Tencon with respect to thermal stability also stabilize the protein against GdmCl induced denaturation.

TABLE 3

| Construct | Mutations | Tm (Kcal) | $[D]_{50\%}$ (M) | DG($H_2O$) (kcal/mol) | SEQ ID NO: |
|---|---|---|---|---|---|
| Tencon | | 78.04 | 3.4 | 12 | 16 |
| Tencon17 | N46V | 81.88 | 3.6 | 12.8 | 17 |
| Tencon18 | E14P | 82.77 | 3.5 | 12.4 | 18 |
| Tencon19 | E11N | 79 | 3.4 | 12 | 19 |
| Tencon20 | E37P | 77.4 | 3.4 | 12 | 20 |
| Tencon21 | G73Y | 67.56 | 2.4 | 8.5 | 21 |
| Tencon22 | E86I | 82.78 | 3.7 | 13.1 | 22 |
| Tencon23 | N46V/E86I | 86.65 | 4.1 | 14.5 | 23 |
| Tencon24 | E14P/N46V/E86I | 87.47 | 4 | 14.2 | 24 |
| Tencon25 | L17A/N46V/E86I | 92.73 | 5.1 | 18.1 | 25 |
| Tencon26 | L17A | 84.9 | 4.6 | 16.2 | 26 |

Size Exclusion Chromatography

Size exclusion chromatography (SEC) was used to assess the aggregation state of Tencon and each Tencon variant. 5 μL of each sample were injected onto a Superdex 75 5/150 column (GE Healthcare) at a flow rate of 0.3 mL/min with a PBS mobile phase. Elution from the column was monitored by absorbance at 280 nm. In order to assess the aggregation state, the column was previously calibrated with globular molecular weight standards (Sigma). All of the samples tested, with the exception of Tencon21, eluted in one peak at an elution volume consistent with that of a monomeric sample. Tencon21 eluted with 2 peaks, indicating the presence of aggregates.

EXAMPLE 3

Generation of Tencon Libraries Having Alternative Binding Surfaces Design of the TCL14 Library The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., *Proc Natl Acad Sci USA*, 104, 6632-6637, 2007). In contrast, an ankyrin repeat scaffold protein that was selected to bind to MBP was found to have a much more planar interaction surface and to bind to the outer surface of MBP distant from the active site (Binz et al., *Nat Biotechnol*, 22, 575-58, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops (FIG. 1) for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure (FIGS. 1, 2A). If the image of the Tencon structure presented in FIG. 1 is rotated by 90 degrees, an alternative surface can be visualized (FIG. 2B). This slightly concave surface is formed by the CD and FG loops and two antiparallel beta-strands, the C and the F beta-strands, and is herein called the C-CD-F-FG surface (FIG. 2B). The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

A new library, herein called TCL14 (SEQ ID NO: 28), was designed into Tencon25 scaffold (SEQ ID NO: 25) having an additional E11R substitution (Tencon27, SEQ ID NO: 27) (FIGS. 2B, 3). Positions of the loops and strands and their sequences are shown in Table 4 and Table 5 for Tencon27 (SEQ ID NO: 27) and TCL14 (SEQ ID NO: 28), respectively. In Table 5, "X" indicates any amino acid.

Tencon27 (SEQ ID NO: 27):
LPAPKNLVVSRVTEDSARLSWTAPDAAFDSFLIQYQESEKVGEAIVLTVP

GSERSYDLTGLKPGTEYTVSIYGVKGGHRSNPLSAIFTT

TCL14 library (SEQ ID NO: 28):
LPAPKNLVVSRVTEDSARLSWTAPDAAFDSFXIXYXEXXXXGEAIVLTVP

GSERSYDLTGLKPGTEYXVXIXGVKGGXXSXPLSAIFTT;

wherein "X" is any amino acid.

Figure 5:
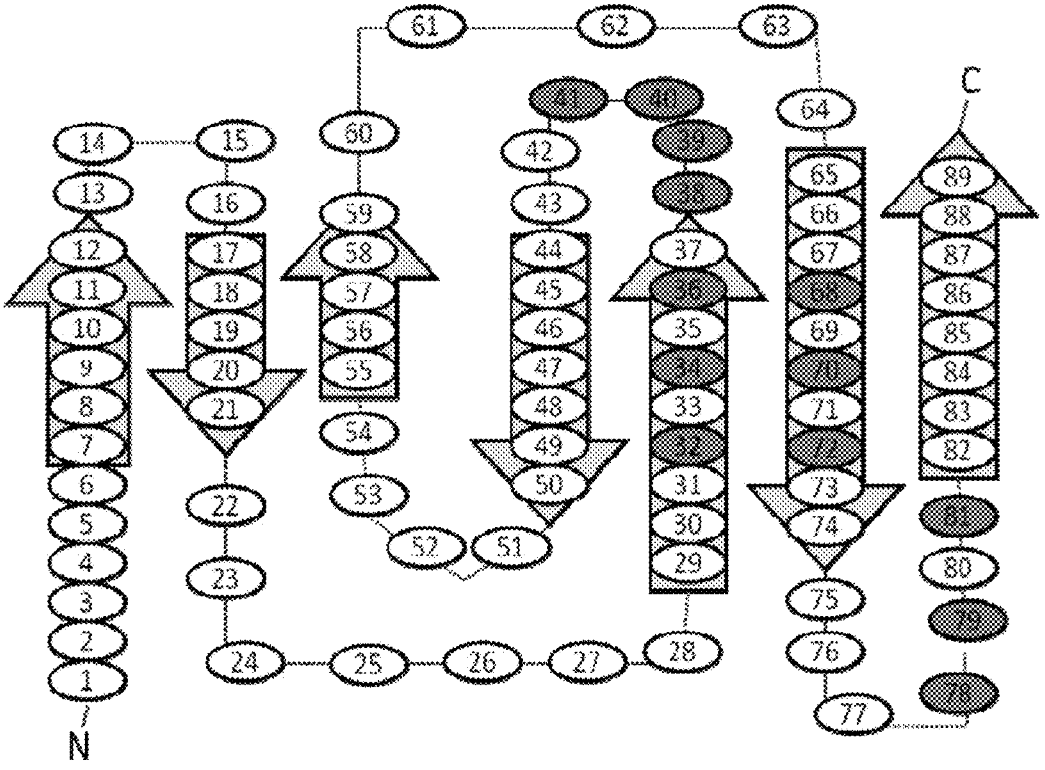
FIG. 5 shows a topology diagram of the library design on Tencon27 (SEQ ID NO: 27) with randomized C-CD-F-FG alternative surface (the TCN14 library). Beta-strands are depicted as arrows with residues of the strands that are hydrogen bonded to one another in the Tencon27 structure placed adjacently in the plot. Positions of residues randomized are depicted with ovals shaded in grey.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81 (FIG. 5). Select residues were chosen for inclusion in the TCL14 design due to the larger theoretical size of the library if all 22 residues were randomized.

Thirteen positions in Tencon27 (SEQ ID NO: 27) were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

TABLE 4

| Region | Amino acid positions (in SEQ ID NO: 27) | Amino acid sequence | SEQ ID NO: |
|---|---|---|---|
| A strand | 1-12 | LPAPKNLVVSRV | 29 |
| AB loop | 13-16 | TEDS | 30 |
| B strand | 17-21 | ARLSW | 31 |
| BC loop | 22-28 | TAPDAAF | 32 |
| C strand | 29-37 | DSFLIQYQE | 33 |
| CD loop | 38-43 | SEKVGE | 34 |
| D strand | 44-50 | AIVLTVP | 35 |
| DE loop | 51-54 | GSER | 36 |
| E strand | 55-59 | SYDLT | 37 |
| EF loop | 60-64 | GLKPG | 38 |
| F strand | 65-74 | TEYTVSIYGV | 39 |
| FG loop | 75-81 | KGGHRSN | 40 |
| G strand | 82-89 | PLSAIFTT | 41 |
| C strand + CD loop | 29-43 | DSFLIQYQESEKVGE | 42 |
| F strand + FG loop | 65-81 | TEYTVSIYGVKGGHRSN | 43 |
| A strand + AB loop + B strand + BC loop | 1-28 | LPAPKNLVVSRVTEDSARLSWTAPDAAF | 44 |

In contrary to existing FN3-scaffold based library designs (Koide, et al., *J Mol Biol*, 284, 1141-1151, 1998; Koide et al., *Proc Natl Acad Sci USA* 104, 6632-6637, 2007; Dineen et al., *BMC Cancer*, 8, 352-361, 2008; Olson and Roberts, *Protein Sci*, 16, 476-484, 2007; Xu et al., *Chemistry & Biology*, 9, 933-942, 2002; Karatan et al., *Chem Biol* 11, 835-844, 2004; Hackel et al., *J Mol Biol*, 401, 84-96, 2010; Hackel et al., *J Mol Biol* 381, 1238-1252, 2008; Koide et al., *Proc Natl Acad Sci USA*, 104, 6632-6637, 2007; Lipovsek et al., *J Mol Biol*, 368, 1024-1041, 2007; Intl. Pat. Pub. No. WO2009/133208; Intl. Pat. Pub. No. WO2009/058379; U.S. Pat. No. 7,115,396), the designed TCL14 library surface has no similarity in structure to that of antibody variable domains or CDRs, or previously described FN3 libraries. Due to the large interaction surface generated by this design, high affinity molecules can be isolated quickly, possibly without the need for affinity maturation steps. Because this design does not

TABLE 5

| Region | Amino acid positions (in SEQ ID NO: 28) | Amino acid sequence | SEQ ID NO: |
|---|---|---|---|
| C strand | 29-37 | DSFXIXYXE | 45 |
| F strand | 65-74 | TEYXVXIXGV | 46 |
| C strand + CD loop | 29-43 | DSFXIXYXEXXXXGE | 47 |
| F strand + FG loop | 65-81 | TEYXVXIXGVKGGXXSX | 48 |
| A strand + AB loop + B strand + BC loop | 1-28 | LPAPKXLXVXXVXXXXAX LXWXAPDAAF | 49 |
| E strand | 55-59 | XYXLT | 50 |

randomize long stretches of consecutive amino acids, it may produce FN3 binding molecules that are more soluble and stable than previously described libraries. The TCL14 library described produces a flat or concave interaction surface in comparison to the curved surface of previous libraries. Thus, FN3 molecules selected from TCL14 are likely to bind to distinct antigens and epitopes as those found from previous FN3 library designs. The TCL14 library design may also allow for the production of two distinct binding surfaces on the same molecule to achieve bi-specificity.

Generation of the TCL14 Library

The TCL14 library described above was expressed using the cis-display system (Odegrip et al., *Proc Natl Acad Sci USA* 101: 2806-2810, 2004). In this system, the library is ligated to DNA fragments encoding the RepA coding sequence, cis and ori elements, and a Tac promoter, and the resulting ligation product is in vitro transcribed/translated. The produced TCL14-RepA fusion proteins are bound in cis to the DNA by which the fusion proteins are encoded. The library is screened for scaffold molecules binding specifically to proteins of interest, the molecules are isolated and the bound DNA amplified to identify the coding sequences of the bound scaffold molecules.

TCL14 library was generated by randomizing positions L32, Q34, Q36 (C-strand), S38, E39, K40, V41 (CD-loop), T68, S70, Y72 (F-strand), H78, R79, and N81 (FG-loop) in Tencon 27 (SEQ ID NO: 27) using the polymerase chain reaction (PCR) with degenerate primers and cloned 5' to the RepA gene for cis-display using standard protocols. The primer C-CD N46V (SEQ ID No. 51) was used to randomize the C strand and the C:D loop and the primer F-FG-Sf E86I-R (SEQ ID No. 52) was used to randomize the F strand and the F:G loop. The final ligation was amplified with the primers R1RecFor (SEQ ID NO: 53) and DigLigRev (SEQ ID NO: 54) to generate the TCL14 library for in vitro transcription/translation. Table 6 shows the sequences of the primers utilized. Codon NNS were used for diversification (IUB code; N indicating A, C, G, or T; S indicating C or G).

TABLE 6

| Primer Name | Sequence | SEQ ID NO |
|---|---|---|
| C-CD N46V | GCGGCGTTCGACTCTTTCNNSATCNNSTACNNSGAANNSNNSNNSNNSG GTGAAGCGATCGGTCTGACCGTTCCGGGTTCTGAACGTTCTTACGACCT GACCGGTCTGAAACCGGGTACCGAATAC | 51 |
| F-FG-Sf E86I-R | GGTGGTGAAGATCGCAGACAGCGGSNNAGASNNSNNACCACCTTTAAC ACCSNNGATSNNAACSNNGTATTCGGTACCCGGTTTCAGACCGGTCAGG TCGTA | 52 |
| R1RecFor | GAACGCGGCTACAATTAATACATAACC | 53 |
| DigLigRev | CATGATTACGCCAAGCTCAGAA | 54 |
| TCON6 | AAGAAGGAGAACCGGTATGCTGCCGGCGCCGAAAAAC | 55 |
| TCON5 E86I short | GAGCCGCCGCCACCGGTTTAATGGTGATGGTGATGGTGACCACCGGTG GTGAAGATCGCAGACAG | 56 |

Characterization of the TCL14 Library

The generated TCL14 library was PCR cloned into a modified pET15 vector (EMD Biosciences) containing a ligase independent cloning site (pET154-LIC) using TCON6 (SEQ ID NO: 55) and TCON5 E86I short (SEQ ID NO: 56) primers, and the proteins were expressed as C-terminal His6-tagged proteins after transformations and IPTG induction (1 mM final, 30° C. for 16 hours) using standard protocols. The cells were harvested by centrifugation and subsequently lysed with Bugbuster HT (EMD Chemicals, Gibbstown, N.J.) supplemented with 0.2 mg/mL Chicken Egg White Lysozyme (Sigma-Aldrich, St. Louis, Mo.). The bacterial lysates were clarified by centrifugation and the supernatants were transferred to new 96 deepwell plates. The proteins were purified using a 96 well Ni-NTA Multitrap Plate (GE Lifesciences, Piscataway, N.J.).

Figure 7:
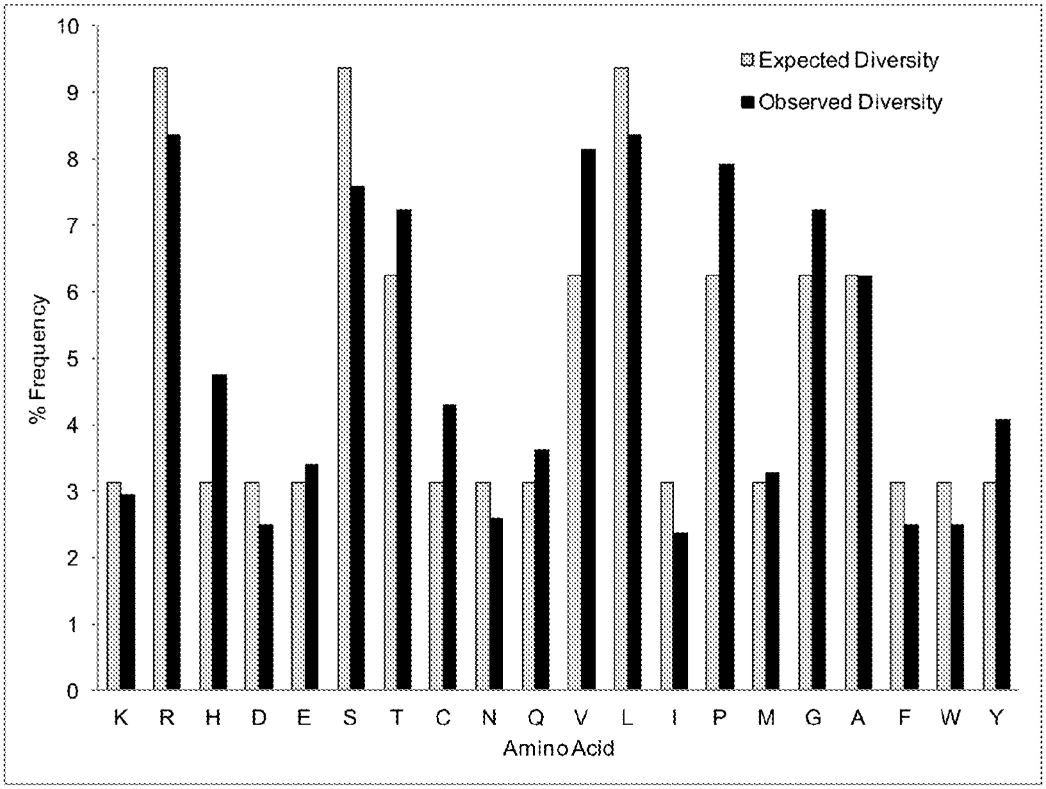
FIG. 7 shows expected and observed amino acid distribution at randomized positions in the TCL14 library.

A random selection of clones was picked and sequences to evaluate obtained distribution in the library. The observed diversity in the library was well in accordance to the expected (FIG. 7). To calculate the observed diversity in the full length library clones, the total number of times a given amino acid appeared in the diversified library regions was counted in all clones and divided by the total number of random positions (13 random library positions * 69 full length clones) and multiplied by 100 to yield % Frequency.

The Expected Diversity is based on the NNS degenerate codon with the following amino acid distribution: Phe=n1, Leu=3, Ile=1, Met=1, Val=2, Ser=3, Pro=2, Thr=2, Ala=2, Cys=1, Arg=3, Gly=2, Tyr=1, His=1, Gln=1, Asn=1, Lys=1, Asp=1, Glu=1, Trp=1 codon(s) divided by the total number of codons (32) multiplied by 100 to yield % Frequency.

Purified proteins were subjected to size exclusion chromatography to determine the aggregation propensity of individual library members. The elution profiles of select clones were determined by injecting 10 μL of the purified proteins onto a Superdex 75 5/150 column using an Agilent 1200 HPLC with absorbance read at 280 nm. ~80% of the non-cysteine containing clones eluted as a single, monomeric peak, thus signifying that the majority individual library members have retained the intrinsic solubility and structure of the parent molecule. Some molecules containing free cysteine were found to oxidize after purification and thus elute as dimeric molecules.

Differential Scanning calorimetry (DSC) was used to further characterize clones that had a monodispersed profile as determined by SEC analysis. DSC data was obtained by heating 0.5 mg/mL solutions for each clone in PBS from 35° C. to 95° C. at a rate of 1° C./min in a VP-DSC capillary cell microcalorimeter (Microcal, LLC, Piscataway, N.J.). Melting temperatures were calculated for each clone using CpCalc (Microcal, LLC, Piscataway, N.J.) software with a summary of the data shown in Table 7. The average melting temperature of the tested molecules was 70±9° C. The obtained data demonstrates that the TCL14 library design produces scaffold molecules that have retained a significant amount of the thermal stability of the parent molecule Tencon25 (93° C.) and are themselves inherently thermally stable and well folded.

TABLE 7

| Clone Number | Tm (° C.) |
|---|---|
| TcCF-003 | 60 |
| TcCF-004 | 61.5 |
| TcCF-006 | 76.3 |
| TcCF-031 | 71.2 |
| TcCF-041 | 71 |
| TcCF-078 | 68 |
| TcCF-082 | 87 |
| TcCF-083 | 72.3 |
| TcCF-084 | 62.3 |
| TcCF-090 | 70.2 |
| TcCF-092 | 71.5 |
| TcCF-103 | 51 |
| TcCF-106 | 87.3 |
| TcCF-107 | 74.5 |
| TcCF-111 | 68 |

Selection of TCL14 Library Molecules Specifically Binding to Target Molecules of Interest The TCL14 library was screened against various target proteins of different protein classes consisting of cell surface receptor extracellular domains, cytokines, kinases, phosphatases, heat shock proteins and immunoglobulins and their fragments to identify scaffold molecules specifically binding to these proteins and/or protein domains. Purified soluble proteins expressed in HEK293 or *E. coli* cells were biotinylated using the EZ-Link No-Weigh Sulfo-NHS-LC-Biotin Microtubes (Thermo Fisher, Rockford, Ill.) followed by extensive dialysis into PBS. For selections, 3 μg of TCL14 library was in vitro transcribed and translated (IVTT) in E. *Coli* S30 Linear Extract (Promega, Madison, Wis.) and the expressed library blocked with Cis Block (2% BSA (Sigma-Aldrich, St. Louis, Mo.), 100 μg/ml Herring Sperm DNA (Promega, Madison, Wis.), 1 mg/mL heparin (Sigma-Aldrich, St. Louis, Mo.). For selection, each biotinylated target protein was added at concentrations of 400 nM (Round 1), 200 nM (Rounds 2 and 3) and 100 nM (Rounds 4 and 5). Bound library members were recovered using neutravidin magnetic beads (Thermo Fisher, Rockford, Ill.) (Rounds 1, 3, and 5) or streptavidin magnetic beads (Promega, Madison, Wis.) (Rounds 2 and 4) and unbound library members were removed by washing the beads 5-14 times with 500 μL PBST followed by 2 washes with 500 μL PBS.

Following 5 rounds of selection, the DNA output was amplified by PCR and subcloned into pET154-LIC using standard protocols.

Additional selection rounds were performed in order to identify scaffold molecules with improved affinities for two target proteins. Briefly, outputs from round 5 were prepared as described above and subjected to additional iterative rounds of selection with the following changes: incubation with biotinylated target protein was decreased from 1 hour to 15 minutes and bead capture was decreased from 20 minutes to 15 minutes, biotinylated target protein decreased to 25 nM (Rounds 6 and 7) or 2.5 nM (Rounds 8 and 9), and an additional 1 hour wash was performed in the presence of an excess of non-biotinylated target protein. The goal of these changes was to simultaneously select for binders with a potentially faster on-rate and a slower off-rate yielding a substantially lower $K_D$. The $9^{th}$ round output was PCR amplified, cloned and expressed as described above.

In Vitro Characterization of Scaffold Molecules Binding to Proteins and/or Protein Domains of Interest Binding Enzyme linked immunosorbant assay (ELISA) was performed on 188 individual clones from the round 5 panning outputs. Maxisorp plates (Nunc, Rochester, N.Y.) were coated with 0.1 μg anti-His antibody (Qiagen, Valencia, Calif.) overnight, washed with Tris-Buffered Saline, pH 7.4 with 0.05% Tween-20 (TBST) and blocked using Starting Block T20 (Thermo Fisher, Rockford, Ill.). Clarified bacterial lysates containing 1 μg/ml $His_6$-tagged TCL14-RepA fusions or a control protein (human serum albumin) were applied onto the wells of the coated plates. The plates were incubated for 1 hour, washed with TBST and the biotinylated protein detected with streptavidin-HRP (Jackson Immunoresearch, West Grove, Pa.) and POD chemiluminescent substrate (Roche, Indianapolis, Ind.) using Molecular Devices M5 plate reader. Performance of the library was assessed by a hit rate. The hit rate was defined as the percent (%) of scaffold molecules having 10-fold luminescence signal above the control signal divided by the total number of clones screened (188). As shown in Table 8, the TLC14 library yielded scaffold molecules with hit rates ranging between 8% to 45% for eight distinct proteins. Cytokine 2 is mouse IL-17A.

TABLE 8

| Target | Hit Rate (%) |
|---|---|
| Ser/Thr Kinase | 37 |
| Receptor ECD | 45 |
| Immunoglobulin | 22 |
| Heat Shock Protein | 18 |
| Cytokine | 6 |
| Immunoglobulin 2 | 42 |
| Cytokine 2 | 18 |
| Phosphatase | 8 |

Characterization of Mouse IL-17A Binders

IL-17A Receptor Inhibition

An inhibition assay was performed to determine if the round 5 and 9 panning outputs against mouse IL-17A (mIL-17A) inhibited binding of mIL-17A to the mIL-17A receptor. Maxisorp plates were coated with 0.2 μg/ml mIL-17A receptor Fc fusion (R&D Systems, Minneapolis, Minn.) overnight, washed with Phosphate-Buffered Saline (PBS), pH 7.4 with 0.05% Tween-20 (TBST) and blocked with 2% BSA, 5% Sucrose in PBS. 10 ng/ml biotinylated-mIL17A (b-mIL-17A) was added into the clarified bacterial lysates diluted 1:50 in 1% BSA in PBS, and the mixtures were incubated for 20 minutes. The blocked plates were washed and the bacterial lysates/b-mIL-17A incubations were transferred onto the plates. The plates were incubated for an additional hour, washed with PB ST, and the biotinylated protein detected with streptavidin-HRP (Jackson Immunoresearch, West Grove, Pa.) and OPD colorimetric substrate (Sigma-Aldrich, St. Louis, Mo.). Absorbance at 490 nm was read using an M5 plate reader (Molecular Devices, Sunnyvale, Calif.) and the data converted to % inhibition. Percent inhibition for mIL-17A:mIL-17 receptor binding was defined as 100−(sample/negative control×100).

Select bacterial lysates containing the scaffold molecules inhibiting the mIL-17A:mIL-17 receptor interaction were further characterized in a dose response inhibition assay using the protocol described above, except that 100 μl of purified TCL14-His (Ni-NTA) fusion proteins were used in the assays between concentrations of 10 μM to 56 pM. IC50 values were calculated from the dose response curves using a sigmoidal dose response fit. As summarized in Table 9, the mIL-17A specific inhibitors have a range of IC50s from ~9 to ~428 pM.

TABLE 9

| Clone ID | $IC_{50}$ (pM) | $k_{on}$ (1/Ms) | $k_{off}$ (1/s) | $K_D$ (M) |
|---|---|---|---|---|
| TP1KR9P61-A2 | 33.93 | 137000 | 3.93E−05 | 2.87E−10 |
| TP1KR9P61-A7 | 55.75 | 82000 | 3.46E−05 | 4.21E−10 |
| TP1KR9P61-E2 | 42.82 | 147000 | 3.96E−05 | 2.70E−10 |
| TP1KR9P61-G4 | 8.83 | 162000 | 5.02E−05 | 3.09E−10 |
| TP1KR9P62-A2 | 261.1 | 408000 | 2.17E−05 | 5.31E−11 |
| TP1KR9P62-C3 | 117.1 | 281000 | 1.05E−05 | 3.74E−11 |
| TP1KR9P62-C6 | 109.1 | 568000 | 1.20E−05 | 2.12E−11 |
| TP1KR9P62-D3 | 91.18 | 110000 | 6.07E−05 | 5.54E−10 |
| TP1KR9P62-D4 | 242 | 105000 | 1.00E−05 | 9.52E−11 |
| TP1KR9P62-D8 | 427.5 | 381000 | 1.48E−05 | 3.89E−11 |
| TP1KR9P62-E3 | 64.16 | 113000 | 5.26E−05 | 4.64E−10 |
| TP1KR9P62-H10 | 301.8 | 438000 | 2.11E−05 | 4.82E−10 |

Affinity Measurements

The affinities of select molecules binding to mIL-17A were measured using surface Plasmon resonance using a ProteOn XPR-36 instrument (Bio-Rad). Purified molecules were directly immobilized on the chip via amine coupling with varying densities (100~300 Rus) at pH 5.0 and a flow rate of 30 μL/min for 5 minutes mIL-17A at 100 nM diluted in a 3-fold concentration series was tested for their binding to different molecules on the chip surface. The dissociation phases for all concentrations of all samples was monitored for 1~2 hours at a flow rate of 100 μL/min depending on their off-rate. A buffer sample was injected to monitor the baseline stability and the surface was not regenerated for further use. The response data for all concentration series for each of the different surfaces of the scaffold molecules selected from the TLC14 library were globally fit to a 1:1 simple langmuir binding model to extract estimates of the kinetic ($k_{on}$, $k_{off}$) and affinity ($K_D$) constants. As summarized in Table 9, affinities of the scaffold molecules specifically binding mIL-17A were at a subnanomolar range. Sequences of select mIL-17A binders are shown in SEQ ID NOS: 85-96, and the sequences of the C and F beta-strands and the CD and the FG loops in Table 10.

TABLE 10

| | C strand | | CD loop | |
|---|---|---|---|---|
| Clone ID | sequence | SEQ ID NO: | sequence | SEQ ID NO: |
| TP1KR9P61-A2 | DSFAIEYFE | 63 | DWWSGE | 67 |
| TP1KR9P61-A7 | DSFAIEYFE | 63 | DWWSGE | 67 |
| TP1KR9P61-E2 | DSFAIEYFE | 63 | DWWSGE | 67 |
| TP1KR9P61-G4 | DSFAIEYFE | 63 | DWWSGE | 67 |
| TP1KR9P62-A2 | DSFAIEYSE | 64 | DYWLGE | 68 |
| TP1KR9P62-C3 | DSFAIEYFE | 63 | DWWSGE | 67 |
| TP1KR9P62-C6 | DSFAIEYFE | 63 | DWWSGE | 67 |
| TP1KR9P62-D3 | DSFAIEYFE | 63 | DWWSGE | 67 |
| TP1KR9P62-D4 | DSFGIIYFE | 65 | DWWAGE | 69 |
| TP1KR9P62-D8 | DSFAIEYFE | 63 | DWWSGE | 67 |
| TP1KR9P62-E3 | DSFGIEYFE | 66 | DYWTGE | 70 |
| TP1KR9P62-H10 | DSFAIEYFE | 63 | DWWSGE | 67 |

| | F strand | | FG loop | |
|---|---|---|---|---|
| Clone ID | sequence | SEQ ID NO: | sequence | SEQ ID NO: |
| TP1KR9P61-A2 | TEYAVSIRGV | 71 | KGGMPSA | 75 |
| TP1KR9P61-A7 | TEYSVSIRGV | 72 | KGGYPSS | 76 |
| TP1KR9P61-E2 | TEYAVSIRGV | 71 | KGGMPSP | 77 |
| TP1KR9P61-G4 | TEYAVSIRGV | 71 | KGGYPSA | 78 |
| TP1KR9P62-A2 | TEYGVSIRGV | 73 | KGGYPSP | 79 |
| TP1KR9P62-C3 | TEYSVTIRGV | 74 | KGGPPSS | 80 |
| TP1KR9P62-C6 | TEYSVTIRGV | 74 | KGGYPSS | 81 |
| TP1KR9P62-D3 | TEYSVSIRGV | 72 | KGGYPSS | 81 |
| TP1KR9P62-D4 | TEYGVSIRGV | 73 | KGGPPSR | 82 |
| TP1KR9P62-D8 | TEYGVSIRGV | 73 | KGGLASP | 83 |
| TP1KR9P62-E3 | TEYAVSIRGV | 71 | KGGYPSA | 78 |
| TP1KR9P62-H10 | TEYSVSIRGV | 72 | KGGHPSV | 84 |

EXAMPLE 4

Tencon27 Libraries Randomized at a Second Alternative Surface

Figure 6:
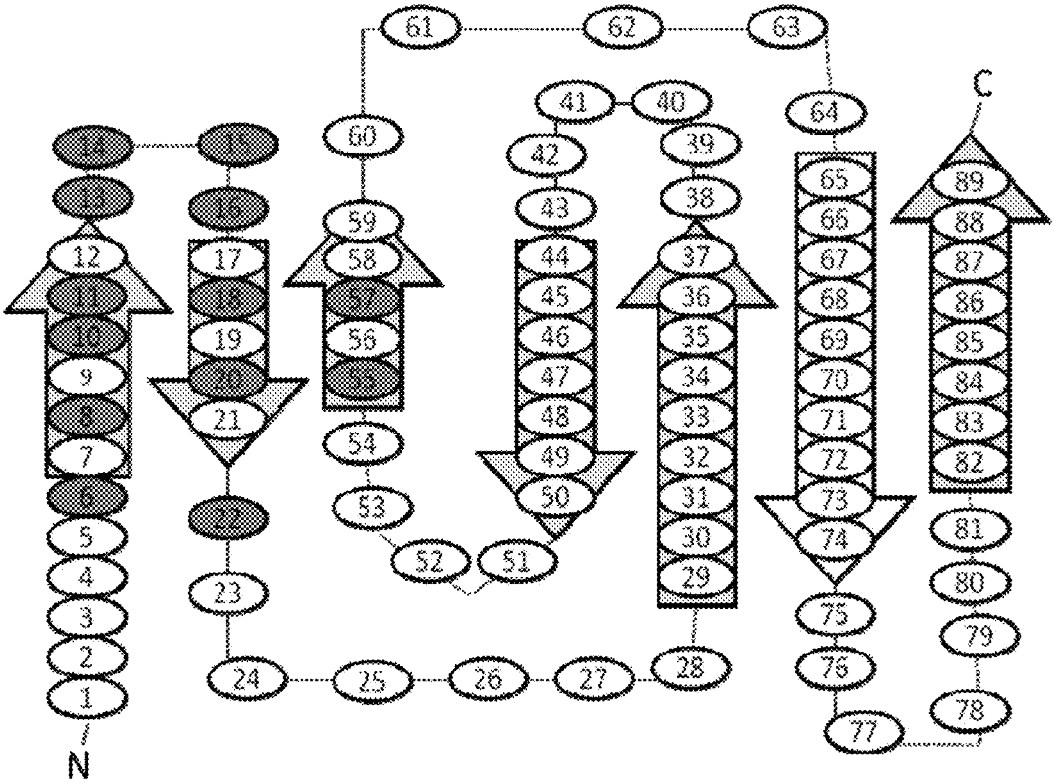
FIG. 6 shows a topology diagram of the library design on Tencon27 (SEQ ID NO: 27) with randomized A-AB-B-BC-E alternative surface (the TCL15 library). Beta-strands are depicted as arrows with residues of the strands that are hydrogen bonded to one another in the tencon structure placed adjacently in the plot. Positions of residues randomized are depicted with ovals shaded in grey.

A second alternative surface on Tencon27 resides on the opposite side of the C-CD-F-FG surface as visualized in FIG. 2C, herein called the A-AB-B-BC-E surface, formed by the A beta-strand, the AB loop, the B beta-strand, the BC loop, and the E beta-strand. The A-AB-B-BC-E surface is also slightly concave, and can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta-strands. By choosing the appropriate residues in the beta-strands, the inherent stability of the Tencon27 scaffold should be minimally compromised while providing a unique scaffold surface for interaction with other proteins. Randomizing the A-AB-B-BC-E surface will produce a binding surface on the opposite side of the Tencon27 structure when compared to the TCL14 library design. The library design on Tencon27 with randomized A-AB-B-BC-E surface is shown in SEQ ID NO: 61 (the TCL15 library) and in FIG. 6.

TCL15 library (SEQ ID NO: 61):
LPAPKXLXVXXVXXXXAXLXWXAPDAAFDSFLIQYQESEKVGEAIVLTVP

GSERXYXLTGLKPGTEYTVSIYGVKGGHRSNPLSAIFTT;

wherein X is any amino acid.

The TCL15 library is generated and selected for scaffolds specifically binding target molecules as described above for the TCL14 library.

EXAMPLE 5

Other FN3 Domains: Generation of Libraries by Randomizing Alternative Surfaces The library designs utilizing alternative surfaces described in the examples for the Tencon27 scaffold can be applied to other FN3 domains of various proteins due to the structural similarity among the FN3 domains. Such FN3 domains may be naturally occurring or synthetic, and are for example a Fibcon consensus scaffold (SEQ ID NO: 58) based on a consensus sequence of fibronectin domains (U.S. Pat. Pub. No. 2010/0255056), the 10$^{th}$ FN3 domain of human fibronectin (FN10) (SEQ ID NO: 97), or the 3$^{rd}$ FN3 domain from human tenascin (TN3) (SEQ ID NO: 3), or any FN3 domain present in proteins listed in Table 1.

Library designs for Fibcon, FN10 and TN3 libraries with randomized C-CD-F-FG alternative surfaces is shown in FIG. 8 and in SEQ ID NOS: 62, 98, and 99, respectively. Designed libraries are synthesized, expressed and selected for specific binders using protocols described within.

Fibcon-based protein scaffold library with randomized C-CD-F-FG surface (SEQ ID NO: 62):

LDAPTDLQVTNVTDTSITVSWTPPSATITGYXIXYXPXXXXGEPKELTVP

PSSTSVTITGLTPGVEYXVXLXALKDNXXSXPLVGTQTT;

wherein X is any amino acid.

FN10-based protein scaffold library with randomized C-CD-F-FG surface (SEQ ID NO: 98):

VSDVPRDLEVVAATPTSLLISWDAPAVTVRYYXIXYXEXXXXSPVQEFTV

PGSKSTATISG LKPGVDYXIXVXAVTGRGDSPXXSXPISINYRT;

wherein X is any amino acid.

TN3-based protein scaffold library with randomized C-CD-F-FG surface (SEQ ID NO: 99):

DAPSQIEVKDVTDTTALITWFKPLAEIDGIXLXYXIXXXXGDRTTIDLTE

DENQYSIGNLKPDTEYXVXLXSRRGDXXSXPAKETFTT;

wherein X is any amino acid.

Similarly to as described for the Tencon27 scaffold, some or all of the residues comprising the CD and/or FG loops of other FN3 domains can be replaced with 1, 2, 3, 4, 5, 6, 7, 8, 9, 10, 11, 12, or 13 randomized positions to generate libraries of different lengths.

It will be clear that the invention can be practiced otherwise than as particularly described in the foregoing description and examples. Numerous modifications and variations of the present invention are possible in light of the above teachings and, therefore, are within the scope of the appended claims.

What is claimed:

1. A method of obtaining a protein scaffold that specifically binds to a target molecule, comprising:

a. contacting or panning a library of fibronectin module of type III (FN3) domains having a diversified C-CD-F-FG alternative surface formed by a C beta-strand, a CD loop, an F beta-strand, and an FG loop with the target molecule, and b. isolating a protein scaffold specifically binding to the target molecule with a predefined affinity, wherein the library is formed by providing a reference FN3 domain polypeptide having the amino acid sequence at least 80% identical to that of SEQ ID NO: 27 and introducing diversity into the reference FN3 domain polypeptide by mutating at least one C beta-strand residue and at least one F beta-strand residue to form the FN3 domain library having the diversified C-CD-F-FG alternative surface, wherein the at least one residue in the C beta-strand is mutated with the proviso that S30 is not mutated (residue numbering according to SEQ ID NO: 27), wherein the at least one residue in the F beta-strand is mutated with the proviso that E66 is not mutated (residue numbering according to SEQ ID NO: 27), wherein each of the C beta-strand residues L32, Q34 and Q36 are mutated (residue numbering according to SEQ ID NO: 27) or each of the F-beta strand residues T68, S70 and Y72 are mutated (residue numbering according to SEQ ID NO: 27).

2. The method of claim 1, wherein 1, 2, 3 or 4 residues in the CD loop residues in the reference FN3 domain polypeptide are mutated with the proviso that G42 and E43are not mutated (residues numbering according to SEQ ID NO: 27).

3. The method of claim 2, wherein the residues S38, E39, K40 and V41 in the CD loop in the reference FN3 domain polypeptide are mutated.

4. The method of claim 3, wherein 1, 2, 3 or 4 residues in the FG loop in the reference FN3 domain polypeptide are mutated with the proviso that the residues K75, G76, G77 and S80 are not mutated (residue numbering according to SEQ ID NO: 27).

5. The method of claim 4, wherein the residues H78, R79 and N81 in the FG loop in the reference FN3 domain polypeptide are mutated (residue numbering according to SEQ ID NO: 27).

6. The method of claim 5, wherein the reference FN3 domain polypepetide comprises an amino acid sequence of SEQ ID NO: 27, optionally comprising at least one substitution at amino acid positions 11, 14, 17, 37, 46, 73, or 86.

7. The method of claim 6, wherein the reference FN3 domain polypeptide comprises an amino acid sequence of SEQ ID NO: 28.

* * * * *

SEQUENCE LISTING

```
<160> NUMBER OF SEQ ID NOS: 101

<210> SEQ ID NO 1
<211> LENGTH: 87
<212> TYPE: PRT
<213> ORGANISM: homo sapiens

<400> SEQUENCE: 1

Ser Pro Pro Lys Asp Leu Val Val Thr Glu Val Thr Glu Glu Thr Val
1               5                   10                  15

Asn Leu Ala Trp Asp Asn Glu Met Arg Val Thr Glu Tyr Leu Val Val
            20                  25                  30

Tyr Thr Pro Thr His Glu Gly Gly Leu Glu Met Gln Phe Arg Val Pro
        35                  40                  45

Gly Asp Gln Thr Ser Thr Ile Ile Gln Glu Leu Glu Pro Gly Val Glu
    50                  55                  60

Tyr Phe Ile Arg Val Phe Ala Ile Leu Glu Asn Lys Lys Ser Ile Pro
65                  70                  75                  80

Val Ser Ala Arg Val Ala Thr
                85
```

-continued

<210> SEQ ID NO 2
<211> LENGTH: 95
<212> TYPE: PRT
<213> ORGANISM: homo sapiens

<400> SEQUENCE: 2

```
Thr Tyr Leu Pro Ala Pro Glu Gly Leu Lys Phe Lys Ser Ile Lys Glu
1               5                   10                  15

Thr Ser Val Glu Val Glu Trp Asp Pro Leu Asp Ile Ala Phe Glu Thr
            20                  25                  30

Trp Glu Ile Ile Phe Arg Asn Met Asn Lys Glu Asp Glu Gly Glu Ile
        35                  40                  45

Thr Lys Ser Leu Arg Arg Pro Glu Thr Ser Tyr Arg Gln Thr Gly Leu
    50                  55                  60

Ala Pro Gly Gln Glu Tyr Glu Ile Ser Leu His Ile Val Lys Asn Asn
65                  70                  75                  80

Thr Arg Gly Pro Gly Leu Lys Arg Val Thr Thr Thr Arg Leu Asp
                85                  90                  95
```

<210> SEQ ID NO 3
<211> LENGTH: 88
<212> TYPE: PRT
<213> ORGANISM: homo sapiens

<400> SEQUENCE: 3

```
Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85
```

<210> SEQ ID NO 4
<211> LENGTH: 100
<212> TYPE: PRT
<213> ORGANISM: homo sapiens

<400> SEQUENCE: 4

```
Thr Gly Leu Asp Ala Pro Arg Asn Leu Arg Arg Val Ser Gln Thr Asp
1               5                   10                  15

Asn Ser Ile Thr Leu Glu Trp Arg Asn Gly Lys Ala Ala Ile Asp Ser
            20                  25                  30

Tyr Arg Ile Lys Tyr Ala Pro Ile Ser Gly Gly Asp His Ala Glu Val
        35                  40                  45

Asp Val Pro Lys Ser Gln Gln Ala Thr Thr Lys Thr Thr Leu Thr Gly
    50                  55                  60

Leu Arg Pro Gly Thr Glu Tyr Gly Ile Gly Val Ser Ala Val Lys Glu
65                  70                  75                  80

Asp Lys Glu Ser Asn Pro Ala Thr Ile Asn Ala Ala Thr Glu Leu Asp
                85                  90                  95
```

```
Thr Pro Lys Asp
            100


<210> SEQ ID NO 5
<211> LENGTH: 88
<212> TYPE: PRT
<213> ORGANISM: homo sapiens

<400> SEQUENCE: 5

Asp Thr Pro Lys Asp Leu Gln Val Ser Glu Thr Ala Glu Thr Ser Leu
1               5                   10                  15

Thr Leu Leu Trp Lys Thr Pro Leu Ala Lys Phe Asp Arg Tyr Arg Leu
            20                  25                  30

Asn Tyr Ser Leu Pro Thr Gly Gln Trp Val Gly Val Gln Leu Pro Arg
        35                  40                  45

Asn Thr Thr Ser Tyr Val Leu Arg Gly Leu Glu Pro Gly Gln Glu Tyr
    50                  55                  60

Asn Val Leu Leu Thr Ala Glu Lys Gly Arg His Lys Ser Lys Pro Ala
65                  70                  75                  80

Lys Ser Lys Pro Ala Arg Val Lys
                85


<210> SEQ ID NO 6
<211> LENGTH: 92
<212> TYPE: PRT
<213> ORGANISM: homo sapiens

<400> SEQUENCE: 6

Gln Ala Pro Glu Leu Glu Asn Leu Thr Val Thr Glu Val Gly Trp Asp
1               5                   10                  15

Gly Leu Arg Leu Asn Trp Thr Ala Ala Asp Gln Ala Tyr Glu His Phe
            20                  25                  30

Ile Ile Gln Val Gln Glu Ala Asn Lys Val Glu Ala Ala Arg Asn Leu
        35                  40                  45

Thr Val Pro Gly Ser Leu Arg Ala Val Asp Ile Pro Gly Leu Lys Ala
    50                  55                  60

Ala Thr Pro Tyr Thr Val Ser Ile Tyr Gly Val Ile Gln Gly Tyr Arg
65                  70                  75                  80

Thr Pro Val Leu Ser Ala Glu Ala Ser Thr Gly Glu
                85                  90


<210> SEQ ID NO 7
<211> LENGTH: 91
<212> TYPE: PRT
<213> ORGANISM: homo sapiens

<400> SEQUENCE: 7

Glu Thr Pro Asn Leu Gly Glu Val Val Val Ala Glu Val Gly Trp Asp
1               5                   10                  15

Ala Leu Lys Leu Asn Trp Thr Ala Pro Glu Gly Ala Tyr Glu Tyr Phe
            20                  25                  30

Phe Ile Gln Val Gln Glu Ala Asp Thr Val Glu Ala Ala Gln Asn Leu
        35                  40                  45

Thr Val Pro Gly Gly Leu Arg Ser Thr Asp Leu Pro Gly Leu Lys Ala
    50                  55                  60

Ala Thr His Tyr Thr Ile Thr Ile Arg Gly Val Thr Gln Asp Phe Ser
65                  70                  75                  80

Thr Thr Pro Leu Ser Val Glu Val Leu Thr Glu
```

85 90

<210> SEQ ID NO 8
<211> LENGTH: 91
<212> TYPE: PRT
<213> ORGANISM: homo sapiens

<400> SEQUENCE: 8

Glu Val Pro Asp Met Gly Asn Leu Thr Val Thr Glu Val Ser Trp Asp
1 5 10 15

Ala Leu Arg Leu Asn Trp Thr Thr Pro Asp Gly Thr Tyr Asp Gln Phe
20 25 30

Thr Ile Gln Val Gln Glu Ala Asp Gln Val Glu Glu Ala His Asn Leu
35 40 45

Thr Val Pro Gly Ser Leu Arg Ser Met Glu Ile Pro Gly Leu Arg Ala
50 55 60

Gly Thr Pro Tyr Thr Val Thr Leu His Gly Glu Val Arg Gly His Ser
65 70 75 80

Thr Arg Pro Leu Ala Val Glu Val Val Thr Glu
85 90

<210> SEQ ID NO 9
<211> LENGTH: 95
<212> TYPE: PRT
<213> ORGANISM: homo sapiens

<400> SEQUENCE: 9

Asp Leu Pro Gln Leu Gly Asp Leu Ala Val Ser Glu Val Gly Trp Asp
1 5 10 15

Gly Leu Arg Leu Asn Trp Thr Ala Ala Asp Asn Ala Tyr Glu His Phe
20 25 30

Val Ile Gln Val Gln Glu Val Asn Lys Val Glu Ala Ala Gln Asn Leu
35 40 45

Thr Leu Pro Gly Ser Leu Arg Ala Val Asp Ile Pro Gly Leu Glu Ala
50 55 60

Ala Thr Pro Tyr Arg Val Ser Ile Tyr Gly Val Ile Arg Gly Tyr Arg
65 70 75 80

Thr Pro Val Leu Ser Ala Glu Ala Ser Thr Ala Lys Glu Pro Glu
85 90 95

<210> SEQ ID NO 10
<211> LENGTH: 91
<212> TYPE: PRT
<213> ORGANISM: homo sapiens

<400> SEQUENCE: 10

Lys Glu Pro Glu Ile Gly Asn Leu Asn Val Ser Asp Ile Thr Pro Glu
1 5 10 15

Ser Phe Asn Leu Ser Trp Met Ala Thr Asp Gly Ile Phe Glu Thr Phe
20 25 30

Thr Ile Glu Ile Ile Asp Ser Asn Arg Leu Leu Glu Thr Val Glu Tyr
35 40 45

Asn Ile Ser Gly Ala Glu Arg Thr Ala His Ile Ser Gly Leu Pro Pro
50 55 60

Ser Thr Asp Phe Ile Val Tyr Leu Ser Gly Leu Ala Pro Ser Ile Arg
65 70 75 80

Thr Lys Thr Ile Ser Ala Thr Ala Thr Thr Glu
85 90

<210> SEQ ID NO 11
<211> LENGTH: 91
<212> TYPE: PRT
<213> ORGANISM: homo sapiens

<400> SEQUENCE: 11

```
Ala Leu Pro Leu Leu Glu Asn Leu Thr Ile Ser Asp Ile Asn Pro Tyr
1               5                   10                  15

Gly Phe Thr Val Ser Trp Met Ala Ser Glu Asn Ala Phe Asp Ser Phe
            20                  25                  30

Leu Val Thr Val Val Asp Ser Gly Lys Leu Leu Asp Pro Gln Glu Phe
        35                  40                  45

Thr Leu Ser Gly Thr Gln Arg Lys Leu Glu Leu Arg Gly Leu Ile Thr
    50                  55                  60

Gly Ile Gly Tyr Glu Val Met Val Ser Gly Phe Thr Gln Gly His Gln
65                  70                  75                  80

Thr Lys Pro Leu Arg Ala Glu Ile Val Thr Glu
                85                  90
```

<210> SEQ ID NO 12
<211> LENGTH: 92
<212> TYPE: PRT
<213> ORGANISM: homosapiens

<400> SEQUENCE: 12

```
Ala Glu Pro Glu Val Asp Asn Leu Leu Val Ser Asp Ala Thr Pro Asp
1               5                   10                  15

Gly Phe Arg Leu Ser Trp Thr Ala Asp Glu Gly Val Phe Asp Asn Phe
            20                  25                  30

Val Leu Lys Ile Arg Asp Thr Lys Lys Gln Ser Glu Pro Leu Glu Ile
        35                  40                  45

Thr Leu Leu Ala Pro Glu Arg Thr Arg Asp Leu Thr Gly Leu Arg Glu
    50                  55                  60

Ala Thr Glu Tyr Glu Ile Glu Leu Tyr Gly Ile Ser Lys Gly Arg Arg
65                  70                  75                  80

Ser Gln Thr Val Ser Ala Ile Ala Thr Thr Ala Met
                85                  90
```

<210> SEQ ID NO 13
<211> LENGTH: 89
<212> TYPE: PRT
<213> ORGANISM: homo sapiens

<400> SEQUENCE: 13

```
Gly Ser Pro Lys Glu Val Ile Phe Ser Asp Ile Thr Glu Asn Ser Ala
1               5                   10                  15

Thr Val Ser Trp Arg Ala Pro Thr Ala Gln Val Glu Ser Phe Arg Ile
            20                  25                  30

Thr Tyr Val Pro Ile Thr Gly Gly Thr Pro Ser Met Val Thr Val Asp
        35                  40                  45

Gly Thr Lys Thr Gln Thr Arg Leu Val Lys Leu Ile Pro Gly Val Glu
    50                  55                  60

Tyr Leu Val Ser Ile Ile Ala Met Lys Gly Phe Glu Glu Ser Glu Pro
65                  70                  75                  80

Val Ser Gly Ser Phe Thr Thr Ala Leu
                85
```

-continued

<210> SEQ ID NO 14
<211> LENGTH: 88
<212> TYPE: PRT
<213> ORGANISM: homo sapiens

<400> SEQUENCE: 14

Asp Gly Pro Ser Gly Leu Val Thr Ala Asn Ile Thr Asp Ser Glu Ala
1               5                   10                  15

Leu Ala Arg Trp Gln Pro Ala Ile Ala Thr Val Asp Ser Tyr Val Ile
            20                  25                  30

Ser Tyr Thr Gly Glu Lys Val Pro Glu Ile Thr Arg Thr Val Ser Gly
        35                  40                  45

Asn Thr Val Glu Tyr Ala Leu Thr Asp Leu Glu Pro Ala Thr Glu Tyr
    50                  55                  60

Thr Leu Arg Ile Phe Ala Glu Lys Gly Pro Gln Lys Ser Ser Thr Ile
65                  70                  75                  80

Thr Ala Lys Phe Thr Thr Asp Leu
                85

<210> SEQ ID NO 15
<211> LENGTH: 89
<212> TYPE: PRT
<213> ORGANISM: homosapiens

<400> SEQUENCE: 15

Asp Ser Pro Arg Asp Leu Thr Ala Thr Glu Val Gln Ser Glu Thr Ala
1               5                   10                  15

Leu Leu Thr Trp Arg Pro Pro Arg Ala Ser Val Thr Gly Tyr Leu Leu
            20                  25                  30

Val Tyr Glu Ser Val Asp Gly Thr Val Lys Glu Val Ile Val Gly Pro
        35                  40                  45

Asp Thr Thr Ser Tyr Ser Leu Ala Asp Leu Ser Pro Ser Thr His Tyr
    50                  55                  60

Thr Ala Lys Ile Gln Ala Leu Asn Gly Pro Leu Arg Ser Asn Met Ile
65                  70                  75                  80

Gln Thr Ile Phe Thr Thr Ile Gly Leu
                85

<210> SEQ ID NO 16
<211> LENGTH: 89
<212> TYPE: PRT
<213> ORGANISM: Artificial Sequence
<220> FEATURE:
<223> OTHER INFORMATION: Consensus FN3 sequence based on tenascin C FN3
      domains

<400> SEQUENCE: 16

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr

85

<210> SEQ ID NO 17
<211> LENGTH: 89
<212> TYPE: PRT
<213> ORGANISM: Artificial sequence
<220> FEATURE:
<223> OTHER INFORMATION: Consensus FN3 sequence based on tenascin C FN3 domains with additional mutations improving stability

<400> SEQUENCE: 17

```
Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85
```

<210> SEQ ID NO 18
<211> LENGTH: 89
<212> TYPE: PRT
<213> ORGANISM: Artificial sequence
<220> FEATURE:
<223> OTHER INFORMATION: Consensus FN3 sequence based on tenascin C FN3 domains with additional mutations improving stability

<400> SEQUENCE: 18

```
Leu Pro Ala Pro Lys Asn Leu Val Val Ser Glu Val Thr Pro Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85
```

<210> SEQ ID NO 19
<211> LENGTH: 89
<212> TYPE: PRT
<213> ORGANISM: Artificial sequence
<220> FEATURE:
<223> OTHER INFORMATION: Consensus FN3 sequence based on tenascin C FN3 domains with additional mutations improving stability

<400> SEQUENCE: 19

```
Leu Pro Ala Pro Lys Asn Leu Val Val Ser Asn Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45
```

-continued

```
Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85


<210> SEQ ID NO 20
<211> LENGTH: 89
<212> TYPE: PRT
<213> ORGANISM: Artificial sequence
<220> FEATURE:
<223> OTHER INFORMATION: Consensus FN3 sequence based on tenascin C FN3
      domains with additional mutations improving stability

<400> SEQUENCE: 20

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Pro Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85


<210> SEQ ID NO 21
<211> LENGTH: 89
<212> TYPE: PRT
<213> ORGANISM: Artificial sequence
<220> FEATURE:
<223> OTHER INFORMATION: Consensus FN3 sequence based on tenascin C FN3
      domains with additional mutations improving stability

<400> SEQUENCE: 21

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Tyr Val Lys Gly Gly His Arg Ser
65                  70                  75                  80

Asn Pro Leu Ser Ala Glu Phe Thr Thr
                85


<210> SEQ ID NO 22
<211> LENGTH: 89
<212> TYPE: PRT
<213> ORGANISM: Artificial sequence
<220> FEATURE:
<223> OTHER INFORMATION: Consensus FN3 sequence based on tenascin C FN3
      domains with additional mutations improving stability

<400> SEQUENCE: 22
```

-continued

```
Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85


<210> SEQ ID NO 23
<211> LENGTH: 89
<212> TYPE: PRT
<213> ORGANISM: Artificial sequence
<220> FEATURE:
<223> OTHER INFORMATION: Consensus FN3 sequence based on tenascin C FN3
      domains with additional mutations improving stability

<400> SEQUENCE: 23

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85


<210> SEQ ID NO 24
<211> LENGTH: 89
<212> TYPE: PRT
<213> ORGANISM: Artificial sequence
<220> FEATURE:
<223> OTHER INFORMATION: Consensus FN3 sequence based on tenascin C FN3
      domains with additional mutations improving stability

<400> SEQUENCE: 24

Leu Pro Ala Pro Lys Asn Leu Val Val Ser Glu Val Thr Pro Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85


<210> SEQ ID NO 25
<211> LENGTH: 89
```

-continued

<212> TYPE: PRT
<213> ORGANISM: Artificial sequence
<220> FEATURE:
<223> OTHER INFORMATION: Consensus FN3 sequence based on tenascin C FN3 domains with additional mutations improving stability

<400> SEQUENCE: 25

```
Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85
```

<210> SEQ ID NO 26
<211> LENGTH: 89
<212> TYPE: PRT
<213> ORGANISM: Artificial sequence
<220> FEATURE:
<223> OTHER INFORMATION: Consensus FN3 sequence based on tenascin C FN3 domains with additional mutations improving stability

<400> SEQUENCE: 26

```
Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85
```

<210> SEQ ID NO 27
<211> LENGTH: 89
<212> TYPE: PRT
<213> ORGANISM: Artificial sequence
<220> FEATURE:
<223> OTHER INFORMATION: Consensus FN3 sequence based on tenascin C FN3 domains with additional mutations improving stability

<400> SEQUENCE: 27

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
```

```
65                  70                  75                  80

Asn Pro Leu Ser Ala Ile Phe Thr Thr
                85


<210> SEQ ID NO 28
<211> LENGTH: 89
<212> TYPE: PRT
<213> ORGANISM: Artificial sequence
<220> FEATURE:
<223> OTHER INFORMATION: TCL14 library based on tencon27 scaffold with
      randomized C-CD-F-FG surface
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(41)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 28

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85


<210> SEQ ID NO 29
<211> LENGTH: 12
<212> TYPE: PRT
<213> ORGANISM: Artificial sequence
<220> FEATURE:
<223> OTHER INFORMATION: Tencon27 scaffold A strand sequence

<400> SEQUENCE: 29
```

-continued

Leu Pro Ala Pro Lys Asn Leu Val Val Ser Arg Val
1               5                   10

<210> SEQ ID NO 30
<211> LENGTH: 4
<212> TYPE: PRT
<213> ORGANISM: Artificial sequence
<220> FEATURE:
<223> OTHER INFORMATION: Tencon27 scaffold AB loop

<400> SEQUENCE: 30

Thr Glu Asp Ser
1

<210> SEQ ID NO 31
<211> LENGTH: 5
<212> TYPE: PRT
<213> ORGANISM: Artificial sequence
<220> FEATURE:
<223> OTHER INFORMATION: Tencon27 scaffold B strand

<400> SEQUENCE: 31

Ala Arg Leu Ser Trp
1               5

<210> SEQ ID NO 32
<211> LENGTH: 7
<212> TYPE: PRT
<213> ORGANISM: Artificial sequence
<220> FEATURE:
<223> OTHER INFORMATION: Tencon27 scaffold BC loop

<400> SEQUENCE: 32

Thr Ala Pro Asp Ala Ala Phe
1               5

<210> SEQ ID NO 33
<211> LENGTH: 9
<212> TYPE: PRT
<213> ORGANISM: Artificial sequence
<220> FEATURE:
<223> OTHER INFORMATION: Tencon27 scaffold C strand

<400> SEQUENCE: 33

Asp Ser Phe Leu Ile Gln Tyr Gln Glu
1               5

<210> SEQ ID NO 34
<211> LENGTH: 6
<212> TYPE: PRT
<213> ORGANISM: Artificial sequence
<220> FEATURE:
<223> OTHER INFORMATION: Tencon27 scaffold CD loop

<400> SEQUENCE: 34

Ser Glu Lys Val Gly Glu
1               5

<210> SEQ ID NO 35
<211> LENGTH: 7
<212> TYPE: PRT
<213> ORGANISM: Artificial sequence
<220> FEATURE:
<223> OTHER INFORMATION: Tencon27 scaffold D strand

<400> SEQUENCE: 35

-continued

Ala Ile Val Leu Thr Val Pro
1 5

<210> SEQ ID NO 36
<211> LENGTH: 4
<212> TYPE: PRT
<213> ORGANISM: Artificial sequence
<220> FEATURE:
<223> OTHER INFORMATION: Tencon27 scaffold DE loop

<400> SEQUENCE: 36

Gly Ser Glu Arg
1

<210> SEQ ID NO 37
<211> LENGTH: 5
<212> TYPE: PRT
<213> ORGANISM: Artificial sequence
<220> FEATURE:
<223> OTHER INFORMATION: Tencon27 scaffold E strand

<400> SEQUENCE: 37

Ser Tyr Asp Leu Thr
1 5

<210> SEQ ID NO 38
<211> LENGTH: 5
<212> TYPE: PRT
<213> ORGANISM: Artificial sequence
<220> FEATURE:
<223> OTHER INFORMATION: Tencon27 scaffold EF loop

<400> SEQUENCE: 38

Gly Leu Lys Pro Gly
1 5

<210> SEQ ID NO 39
<211> LENGTH: 10
<212> TYPE: PRT
<213> ORGANISM: Artificial sequence
<220> FEATURE:
<223> OTHER INFORMATION: Tencon27 scaffold F strand

<400> SEQUENCE: 39

Thr Glu Tyr Thr Val Ser Ile Tyr Gly Val
1 5 10

<210> SEQ ID NO 40
<211> LENGTH: 7
<212> TYPE: PRT
<213> ORGANISM: Artificial sequence
<220> FEATURE:
<223> OTHER INFORMATION: Tencon27 scaffold FG loop

<400> SEQUENCE: 40

Lys Gly Gly His Arg Ser Asn
1 5

<210> SEQ ID NO 41
<211> LENGTH: 8
<212> TYPE: PRT
<213> ORGANISM: Artificial sequence
<220> FEATURE:
<223> OTHER INFORMATION: Tencon27 scaffold G strand

<400> SEQUENCE: 41

Pro Leu Ser Ala Ile Phe Thr Thr 1 5

<210> SEQ ID NO 42
<211> LENGTH: 15
<212> TYPE: PRT
<213> ORGANISM: Artificial sequence
<220> FEATURE:
<223> OTHER INFORMATION: Tencon27 scaffold C strand and CD loop

<400> SEQUENCE: 42

Asp Ser Phe Leu Ile Gln Tyr Gln Glu Ser Glu Lys Val Gly Glu
1 5 10 15

<210> SEQ ID NO 43
<211> LENGTH: 17
<212> TYPE: PRT
<213> ORGANISM: Artificial sequence
<220> FEATURE:
<223> OTHER INFORMATION: Tencon27 scaffold F strand and FG loop

<400> SEQUENCE: 43

Thr Glu Tyr Thr Val Ser Ile Tyr Gly Val Lys Gly Gly His Arg Ser
1 5 10 15

Asn

<210> SEQ ID NO 44
<211> LENGTH: 28
<212> TYPE: PRT
<213> ORGANISM: Artificial sequence
<220> FEATURE:
<223> OTHER INFORMATION: Tencon27 scaffold A strand, AB loop, B strand and BC loop

<400> SEQUENCE: 44

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe
20 25

<210> SEQ ID NO 45
<211> LENGTH: 9
<212> TYPE: PRT
<213> ORGANISM: Artificial sequence
<220> FEATURE:
<223> OTHER INFORMATION: TCL14 library C strand
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 45

Asp Ser Phe Xaa Ile Xaa Tyr Xaa Glu
1 5

<210> SEQ ID NO 46
<211> LENGTH: 10
<212> TYPE: PRT
<213> ORGANISM: Artificial sequence
<220> FEATURE:
<223> OTHER INFORMATION: TCL14 library F strand
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 46

Thr Glu Tyr Xaa Val Xaa Ile Xaa Gly Val
1 5 10

<210> SEQ ID NO 47
<211> LENGTH: 15
<212> TYPE: PRT
<213> ORGANISM: Artificial sequence
<220> FEATURE:
<223> OTHER INFORMATION: TCL14 library C strand and CD loop
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid

<400> SEQUENCE: 47

Asp Ser Phe Xaa Ile Xaa Tyr Xaa Glu Xaa Xaa Xaa Xaa Gly Glu
1 5 10 15

<210> SEQ ID NO 48
<211> LENGTH: 17
<212> TYPE: PRT
<213> ORGANISM: Artificial sequence
<220> FEATURE:
<223> OTHER INFORMATION: TCL14 library F strand and FG loop
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 48

Thr Glu Tyr Xaa Val Xaa Ile Xaa Gly Val Lys Gly Gly Xaa Xaa Ser
1 5 10 15

Xaa

<210> SEQ ID NO 49
<211> LENGTH: 28
<212> TYPE: PRT
<213> ORGANISM: Artificial sequence
<220> FEATURE:
<223> OTHER INFORMATION: TCL15 library A strand, AB loop, B strand and
BC loop
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 49

```
Leu Pro Ala Pro Lys Xaa Leu Xaa Val Xaa Xaa Val Xaa Xaa Xaa Xaa
1               5                   10                  15

Ala Xaa Leu Xaa Trp Xaa Ala Pro Asp Ala Ala Phe
            20                  25
```

<210> SEQ ID NO 50
<211> LENGTH: 5
<212> TYPE: PRT
<213> ORGANISM: Artificial sequence
<220> FEATURE:
<223> OTHER INFORMATION: TCL15 library E strand
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 50

```
Xaa Tyr Xaa Leu Thr
1               5
```

<210> SEQ ID NO 51
<211> LENGTH: 126
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (19)..(20)

<223> OTHER INFORMATION: n is a, c, g, or t
<220> FEATURE:
<221> NAME/KEY: misc_feature
<222> LOCATION: (21)..(21)
<223> OTHER INFORMATION: s is g or c
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (27)..(27)
<223> OTHER INFORMATION: s is g or c
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (33)..(33)
<223> OTHER INFORMATION: s is g or c
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (39)..(39)
<223> OTHER INFORMATION: s is g or c
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: s is g or c
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: s is g or c
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: s is g or c

<400> SEQUENCE: 51
gcggcgttcg actctttcnn satcnnstac nnsgaannsn nsnnsnnsgg tgaagcgatc 60
ggtctgaccg ttccgggttc tgaacgttct tacgacctga ccggtctgaa accgggtacc 120
gaatac 126

<210> SEQ ID NO 52
<211> LENGTH: 102
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (25)..(25)
<223> OTHER INFORMATION: s is c or g
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (31)..(31)
<223> OTHER INFORMATION: s is c or g
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: s is c or g
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (52)..(52)
<223> OTHER INFORMATION: s is c or g
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (58)..(58)
<223> OTHER INFORMATION: s is c or g
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (64)..(64)
<223> OTHER INFORMATION: s is c or g
<220> FEATURE:
<221> NAME/KEY: misc_feature
<222> LOCATION: (65)..(66)
<223> OTHER INFORMATION: n is a, c, g, or t

<400> SEQUENCE: 52
ggtggtgaag atcgcagaca gcggsnnaga snnsnnacca cctttaacac csnngatsnn 60
aacsnngtat tcggtacccg gtttcagacc ggtcaggtcg ta 102

<210> SEQ ID NO 53
<211> LENGTH: 27
<212> TYPE: DNA
<213> ORGANISM: Artificial sequence
<220> FEATURE:
<223> OTHER INFORMATION: primer

<400> SEQUENCE: 53
gaacgcggct acaattaata cataacc 27

<210> SEQ ID NO 54
<211> LENGTH: 22
<212> TYPE: DNA
<213> ORGANISM: Artificial sequence
<220> FEATURE:
<223> OTHER INFORMATION: primer

<400> SEQUENCE: 54
catgattacg ccaagctcag aa 22

<210> SEQ ID NO 55
<211> LENGTH: 37
<212> TYPE: DNA
<213> ORGANISM: Artificial sequence
<220> FEATURE:
<223> OTHER INFORMATION: primer

<400> SEQUENCE: 55
aagaaggaga accggtatgc tgccggcgcc gaaaaac 37

<210> SEQ ID NO 56
<211> LENGTH: 65
<212> TYPE: DNA
<213> ORGANISM: Artificial sequence
<220> FEATURE:
<223> OTHER INFORMATION: primer

<400> SEQUENCE: 56
gagccgccgc caccggttta atggtgatgg tgatggtgac caccggtggt gaagatcgca 60
gacag 65

<210> SEQ ID NO 57
<211> LENGTH: 2201
<212> TYPE: PRT
<213> ORGANISM: homo sapiens

<400> SEQUENCE: 57

Met Gly Ala Met Thr Gln Leu Leu Ala Gly Val Phe Leu Ala Phe Leu
1 5 10 15

Ala Leu Ala Thr Glu Gly Gly Val Leu Lys Lys Val Ile Arg His Lys
20 25 30

Arg Gln Ser Gly Val Asn Ala Thr Leu Pro Glu Glu Asn Gln Pro Val
35 40 45

Val Phe Asn His Val Tyr Asn Ile Lys Leu Pro Val Gly Ser Gln Cys
50 55 60

Ser Val Asp Leu Glu Ser Ala Ser Gly Glu Lys Asp Leu Ala Pro Pro
65 70 75 80

Ser Glu Pro Ser Glu Ser Phe Gln Glu His Thr Val Asp Gly Glu Asn
85 90 95

Gln Ile Val Phe Thr His Arg Ile Asn Ile Pro Arg Arg Ala Cys Gly
100 105 110

Cys Ala Ala Ala Pro Asp Val Lys Glu Leu Leu Ser Arg Leu Glu Glu
115 120 125

Leu Glu Asn Leu Val Ser Ser Leu Arg Glu Gln Cys Thr Ala Gly Ala
130 135 140

Gly Cys Cys Leu Gln Pro Ala Thr Gly Arg Leu Asp Thr Arg Pro Phe
145 150 155 160

Cys Ser Gly Arg Gly Asn Phe Ser Thr Glu Gly Cys Gly Cys Val Cys
165 170 175

Glu Pro Gly Trp Lys Gly Pro Asn Cys Ser Glu Pro Glu Cys Pro Gly
180 185 190

Asn Cys His Leu Arg Gly Arg Cys Ile Asp Gly Gln Cys Ile Cys Asp
195 200 205

Asp Gly Phe Thr Gly Glu Asp Cys Ser Gln Leu Ala Cys Pro Ser Asp
210 215 220

Cys Asn Asp Gln Gly Lys Cys Val Asn Gly Val Cys Ile Cys Phe Glu
225 230 235 240

Gly Tyr Ala Gly Ala Asp Cys Ser Arg Glu Ile Cys Pro Val Pro Cys
245 250 255

Ser Glu Glu His Gly Thr Cys Val Asp Gly Leu Cys Val Cys His Asp
260 265 270

Gly Phe Ala Gly Asp Asp Cys Asn Lys Pro Leu Cys Leu Asn Asn Cys
275 280 285

Tyr Asn Arg Gly Arg Cys Val Glu Asn Glu Cys Val Cys Asp Glu Gly

-continued

```
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Lys Pro Thr Cys Pro His Ala Cys His Thr
            340                 345                 350

Gln Gly Arg Cys Glu Glu Gly Gln Cys Val Cys Asp Glu Gly Phe Ala
        355                 360                 365

Gly Val Asp Cys Ser Glu Lys Arg Cys Pro Ala Asp Cys His Asn Arg
    370                 375                 380

Gly Arg Cys Val Asp Gly Arg Cys Glu Cys Asp Asp Gly Phe Thr Gly
385                 390                 395                 400

Ala Asp Cys Gly Glu Leu Lys Cys Pro Asn Gly Cys Ser Gly His Gly
                405                 410                 415

Arg Cys Val Asn Gly Gln Cys Val Cys Asp Glu Gly Tyr Thr Gly Glu
            420                 425                 430

Asp Cys Ser Gln Leu Arg Cys Pro Asn Asp Cys His Ser Arg Gly Arg
        435                 440                 445

Cys Val Glu Gly Lys Cys Val Cys Glu Gln Gly Phe Lys Gly Tyr Asp
    450                 455                 460

Cys Ser Asp Met Ser Cys Pro Asn Asp Cys His Gln His Gly Arg Cys
465                 470                 475                 480

Val Asn Gly Met Cys Val Cys Asp Asp Gly Tyr Thr Gly Glu Asp Cys
                485                 490                 495

Arg Asp Arg Gln Cys Pro Arg Asp Cys Ser Asn Arg Gly Leu Cys Val
            500                 505                 510

Asp Gly Gln Cys Val Cys Glu Asp Gly Phe Thr Gly Pro Asp Cys Ala
        515                 520                 525

Glu Leu Ser Cys Pro Asn Asp Cys His Gly Gln Gly Arg Cys Val Asn
    530                 535                 540

Gly Gln Cys Val Cys His Glu Gly Phe Met Gly Lys Asp Cys Lys Glu
545                 550                 555                 560

Gln Arg Cys Pro Ser Asp Cys His Gly Gln Gly Arg Cys Val Asp Gly
                565                 570                 575

Gln Cys Ile Cys His Glu Gly Phe Thr Gly Leu Asp Cys Gly Gln His
            580                 585                 590

Ser Cys Pro Ser Asp Cys Asn Asn Leu Gly Gln Cys Val Ser Gly Arg
        595                 600                 605

Cys Ile Cys Asn Glu Gly Tyr Ser Gly Glu Asp Cys Ser Glu Val Ser
    610                 615                 620

Pro Pro Lys Asp Leu Val Val Thr Glu Val Thr Glu Glu Thr Val Asn
625                 630                 635                 640

Leu Ala Trp Asp Asn Glu Met Arg Val Thr Glu Tyr Leu Val Val Tyr
                645                 650                 655

Thr Pro Thr His Glu Gly Gly Leu Glu Met Gln Phe Arg Val Pro Gly
            660                 665                 670

Asp Gln Thr Ser Thr Ile Ile Gln Glu Leu Glu Pro Gly Val Glu Tyr
        675                 680                 685

Phe Ile Arg Val Phe Ala Ile Leu Glu Asn Lys Lys Ser Ile Pro Val
    690                 695                 700

Ser Ala Arg Val Ala Thr Tyr Leu Pro Ala Pro Glu Gly Leu Lys Phe
705                 710                 715                 720
```

```
Lys Ser Ile Lys Glu Thr Ser Val Glu Val Glu Trp Asp Pro Leu Asp
                725                 730                 735

Ile Ala Phe Glu Thr Trp Glu Ile Ile Phe Arg Asn Met Asn Lys Glu
            740                 745                 750

Asp Glu Gly Glu Ile Thr Lys Ser Leu Arg Arg Pro Glu Thr Ser Tyr
        755                 760                 765

Arg Gln Thr Gly Leu Ala Pro Gly Gln Glu Tyr Glu Ile Ser Leu His
    770                 775                 780

Ile Val Lys Asn Asn Thr Arg Gly Pro Gly Leu Lys Arg Val Thr Thr
785                 790                 795                 800

Thr Arg Leu Asp Ala Pro Ser Gln Ile Glu Val Lys Asp Val Thr Asp
                805                 810                 815

Thr Thr Ala Leu Ile Thr Trp Phe Lys Pro Leu Ala Glu Ile Asp Gly
            820                 825                 830

Ile Glu Leu Thr Tyr Gly Ile Lys Asp Val Pro Gly Asp Arg Thr Thr
        835                 840                 845

Ile Asp Leu Thr Glu Asp Glu Asn Gln Tyr Ser Ile Gly Asn Leu Lys
    850                 855                 860

Pro Asp Thr Glu Tyr Glu Val Ser Leu Ile Ser Arg Arg Gly Asp Met
865                 870                 875                 880

Ser Ser Asn Pro Ala Lys Glu Thr Phe Thr Thr Gly Leu Asp Ala Pro
                885                 890                 895

Arg Asn Leu Arg Arg Val Ser Gln Thr Asp Asn Ser Ile Thr Leu Glu
            900                 905                 910

Trp Arg Asn Gly Lys Ala Ala Ile Asp Ser Tyr Arg Ile Lys Tyr Ala
        915                 920                 925

Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
                965                 970                 975

Ala Thr Ile Asn Ala Ala Thr Glu Leu Asp Thr Pro Lys Asp Leu Gln
            980                 985                 990

Val Ser Glu Thr Ala Glu Thr Ser  Leu Thr Leu Leu Trp  Lys Thr Pro
        995                 1000                1005

Leu Ala  Lys Phe Asp Arg Tyr  Arg Leu Asn Tyr Ser  Leu Pro Thr
    1010                1015                1020

Gly Gln  Trp Val Gly Val Gln  Leu Pro Arg Asn Thr  Thr Ser Tyr
    1025                1030                1035

Val Leu  Arg Gly Leu Glu Pro  Gly Gln Glu Tyr Asn  Val Leu Leu
    1040                1045                1050

Thr Ala  Glu Lys Gly Arg His  Lys Ser Lys Pro Ala  Arg Val Lys
    1055                1060                1065

Ala Ser  Thr Glu Gln Ala Pro  Glu Leu Glu Asn Leu  Thr Val Thr
    1070                1075                1080

Glu Val  Gly Trp Asp Gly Leu  Arg Leu Asn Trp Thr  Ala Ala Asp
    1085                1090                1095

Gln Ala  Tyr Glu His Phe Ile  Ile Gln Val Gln Glu  Ala Asn Lys
    1100                1105                1110

Val Glu  Ala Ala Arg Asn Leu  Thr Val Pro Gly Ser  Leu Arg Ala
    1115                1120                1125
```

```
Val Asp  Ile Pro Gly Leu Lys  Ala Ala Thr Pro Tyr  Thr Val Ser
    1130                 1135                 1140

Ile Tyr  Gly Val Ile Gln Gly  Tyr Arg Thr Pro Val  Leu Ser Ala
    1145                 1150                 1155

Glu Ala  Ser Thr Gly Glu Thr  Pro Asn Leu Gly Glu  Val Val Val
    1160                 1165                 1170

Ala Glu  Val Gly Trp Asp Ala  Leu Lys Leu Asn Trp  Thr Ala Pro
    1175                 1180                 1185

Glu Gly  Ala Tyr Glu Tyr Phe  Phe Ile Gln Val Gln  Glu Ala Asp
    1190                 1195                 1200

Thr Val  Glu Ala Ala Gln Asn  Leu Thr Val Pro Gly  Gly Leu Arg
    1205                 1210                 1215

Ser Thr  Asp Leu Pro Gly Leu  Lys Ala Ala Thr His  Tyr Thr Ile
    1220                 1225                 1230

Thr Ile  Arg Gly Val Thr Gln  Asp Phe Ser Thr Thr  Pro Leu Ser
    1235                 1240                 1245

Val Glu  Val Leu Thr Glu Glu  Val Pro Asp Met Gly  Asn Leu Thr
    1250                 1255                 1260

Val Thr  Glu Val Ser Trp Asp  Ala Leu Arg Leu Asn  Trp Thr Thr
    1265                 1270                 1275

Pro Asp  Gly Thr Tyr Asp Gln  Phe Thr Ile Gln Val  Gln Glu Ala
    1280                 1285                 1290

Asp Gln  Val Glu Glu Ala His  Asn Leu Thr Val Pro  Gly Ser Leu
    1295                 1300                 1305

Arg Ser  Met Glu Ile Pro Gly  Leu Arg Ala Gly Thr  Pro Tyr Thr
    1310                 1315                 1320

Val Thr  Leu His Gly Glu Val  Arg Gly His Ser Thr  Arg Pro Leu
    1325                 1330                 1335

Ala Val  Glu Val Val Thr Glu  Asp Leu Pro Gln Leu  Gly Asp Leu
    1340                 1345                 1350

Ala Val  Ser Glu Val Gly Trp  Asp Gly Leu Arg Leu  Asn Trp Thr
    1355                 1360                 1365

Ala Ala  Asp Asn Ala Tyr Glu  His Phe Val Ile Gln  Val Gln Glu
    1370                 1375                 1380

Val Asn  Lys Val Glu Ala Ala  Gln Asn Leu Thr Leu  Pro Gly Ser
    1385                 1390                 1395

Leu Arg  Ala Val Asp Ile Pro  Gly Leu Glu Ala Ala  Thr Pro Tyr
    1400                 1405                 1410

Arg Val  Ser Ile Tyr Gly Val  Ile Arg Gly Tyr Arg  Thr Pro Val
    1415                 1420                 1425

Leu Ser  Ala Glu Ala Ser Thr  Ala Lys Glu Pro Glu  Ile Gly Asn
    1430                 1435                 1440

Leu Asn  Val Ser Asp Ile Thr  Pro Glu Ser Phe Asn  Leu Ser Trp
    1445                 1450                 1455

Met Ala  Thr Asp Gly Ile Phe  Glu Thr Phe Thr Ile  Glu Ile Ile
    1460                 1465                 1470

Asp Ser  Asn Arg Leu Leu Glu  Thr Val Glu Tyr Asn  Ile Ser Gly
    1475                 1480                 1485

Ala Glu  Arg Thr Ala His Ile  Ser Gly Leu Pro Pro  Ser Thr Asp
    1490                 1495                 1500

Phe Ile  Val Tyr Leu Ser Gly  Leu Ala Pro Ser Ile  Arg Thr Lys
    1505                 1510                 1515

Thr Ile  Ser Ala Thr Ala Thr  Thr Glu Ala Leu Pro  Leu Leu Glu
```

```
    1520                1525                1530

Asn Leu  Thr Ile Ser Asp Ile  Asn Pro Tyr Gly Phe  Thr Val Ser
    1535                1540                1545

Trp Met  Ala Ser Glu Asn Ala  Phe Asp Ser Phe Leu  Val Thr Val
    1550                1555                1560

Val Asp  Ser Gly Lys Leu Leu  Asp Pro Gln Glu Phe  Thr Leu Ser
    1565                1570                1575

Gly Thr  Gln Arg Lys Leu Glu  Leu Arg Gly Leu Ile  Thr Gly Ile
    1580                1585                1590

Gly Tyr  Glu Val Met Val Ser  Gly Phe Thr Gln Gly  His Gln Thr
    1595                1600                1605

Lys Pro  Leu Arg Ala Glu Ile  Val Thr Glu Ala Glu  Pro Glu Val
    1610                1615                1620

Asp Asn  Leu Leu Val Ser Asp  Ala Thr Pro Asp Gly  Phe Arg Leu
    1625                1630                1635

Ser Trp  Thr Ala Asp Glu Gly  Val Phe Asp Asn Phe  Val Leu Lys
    1640                1645                1650

Ile Arg  Asp Thr Lys Lys Gln  Ser Glu Pro Leu Glu  Ile Thr Leu
    1655                1660                1665

Leu Ala  Pro Glu Arg Thr Arg  Asp Ile Thr Gly Leu  Arg Glu Ala
    1670                1675                1680

Thr Glu  Tyr Glu Ile Glu Leu  Tyr Gly Ile Ser Lys  Gly Arg Arg
    1685                1690                1695

Ser Gln  Thr Val Ser Ala Ile  Ala Thr Thr Ala Met  Gly Ser Pro
    1700                1705                1710

Lys Glu  Val Ile Phe Ser Asp  Ile Thr Glu Asn Ser  Ala Thr Val
    1715                1720                1725

Ser Trp  Arg Ala Pro Thr Ala  Gln Val Glu Ser Phe  Arg Ile Thr
    1730                1735                1740

Tyr Val  Pro Ile Thr Gly Gly  Thr Pro Ser Met Val  Thr Val Asp
    1745                1750                1755

Gly Thr  Lys Thr Gln Thr Arg  Leu Val Lys Leu Ile  Pro Gly Val
    1760                1765                1770

Glu Tyr  Leu Val Ser Ile Ile  Ala Met Lys Gly Phe  Glu Glu Ser
    1775                1780                1785

Glu Pro  Val Ser Gly Ser Phe  Thr Thr Ala Leu Asp  Gly Pro Ser
    1790                1795                1800

Gly Leu  Val Thr Ala Asn Ile  Thr Asp Ser Glu Ala  Leu Ala Arg
    1805                1810                1815

Trp Gln  Pro Ala Ile Ala Thr  Val Asp Ser Tyr Val  Ile Ser Tyr
    1820                1825                1830

Thr Gly  Glu Lys Val Pro Glu  Ile Thr Arg Thr Val  Ser Gly Asn
    1835                1840                1845

Thr Val  Glu Tyr Ala Leu Thr  Asp Leu Glu Pro Ala  Thr Glu Tyr
    1850                1855                1860

Thr Leu  Arg Ile Phe Ala Glu  Lys Gly Pro Gln Lys  Ser Ser Thr
    1865                1870                1875

Ile Thr  Ala Lys Phe Thr Thr  Asp Leu Asp Ser Pro  Arg Asp Leu
    1880                1885                1890

Thr Ala  Thr Glu Val Gln Ser  Glu Thr Ala Leu Leu  Thr Trp Arg
    1895                1900                1905

Pro Pro  Arg Ala Ser Val Thr  Gly Tyr Leu Leu Val  Tyr Glu Ser
    1910                1915                1920
```

-continued

Val Asp Gly Thr Val Lys Glu Val Ile Val Gly Pro Asp Thr Thr
1925 1930 1935

Ser Tyr Ser Leu Ala Asp Leu Ser Pro Ser Thr His Tyr Thr Ala
1940 1945 1950

Lys Ile Gln Ala Leu Asn Gly Pro Leu Arg Ser Asn Met Ile Gln
1955 1960 1965

Thr Ile Phe Thr Thr Ile Gly Leu Leu Tyr Pro Phe Pro Lys Asp
1970 1975 1980

Cys Ser Gln Ala Met Leu Asn Gly Asp Thr Thr Ser Gly Leu Tyr
1985 1990 1995

Thr Ile Tyr Leu Asn Gly Asp Lys Ala Glu Ala Leu Glu Val Phe
2000 2005 2010

Cys Asp Met Thr Ser Asp Gly Gly Gly Trp Ile Val Phe Leu Arg
2015 2020 2025

Arg Lys Asn Gly Arg Glu Asn Phe Tyr Gln Asn Trp Lys Ala Tyr
2030 2035 2040

Ala Ala Gly Phe Gly Asp Arg Arg Glu Glu Phe Trp Leu Gly Leu
2045 2050 2055

Asp Asn Leu Asn Lys Ile Thr Ala Gln Gly Gln Tyr Glu Leu Arg
2060 2065 2070

Val Asp Leu Arg Asp His Gly Glu Thr Ala Phe Ala Val Tyr Asp
2075 2080 2085

Lys Phe Ser Val Gly Asp Ala Lys Thr Arg Tyr Lys Leu Lys Val
2090 2095 2100

Glu Gly Tyr Ser Gly Thr Ala Gly Asp Ser Met Ala Tyr His Asn
2105 2110 2115

Gly Arg Ser Phe Ser Thr Phe Asp Lys Asp Thr Asp Ser Ala Ile
2120 2125 2130

Thr Asn Cys Ala Leu Ser Tyr Lys Gly Ala Phe Trp Tyr Arg Asn
2135 2140 2145

Cys His Arg Val Asn Leu Met Gly Arg Tyr Gly Asp Asn Asn His
2150 2155 2160

Ser Gln Gly Val Asn Trp Phe His Trp Lys Gly His Glu His Ser
2165 2170 2175

Ile Gln Phe Ala Glu Met Lys Leu Arg Pro Ser Asn Phe Arg Asn
2180 2185 2190

Leu Glu Gly Arg Arg Lys Arg Ala
2195 2200

<210> SEQ ID NO 58
<211> LENGTH: 89
<212> TYPE: PRT
<213> ORGANISM: Artificial sequence
<220> FEATURE:
<223> OTHER INFORMATION: FN3 scaffold based on consensuns fibronecting FN3 domains

<400> SEQUENCE: 58

Leu Asp Ala Pro Thr Asp Leu Gln Val Thr Asn Val Thr Asp Thr Ser
1 5 10 15

Ile Thr Val Ser Trp Thr Pro Pro Ser Ala Thr Ile Thr Gly Tyr Arg
20 25 30

Ile Thr Tyr Thr Pro Ser Asn Gly Pro Gly Glu Pro Lys Glu Leu Thr
35 40 45

Val Pro Pro Ser Ser Thr Ser Val Thr Ile Thr Gly Leu Thr Pro Gly

```
        50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85


<210> SEQ ID NO 59
<211> LENGTH: 267
<212> TYPE: DNA
<213> ORGANISM: Artificial sequence
<220> FEATURE:
<223> OTHER INFORMATION: cDNA encoding tencon scaffold

<400> SEQUENCE: 59

ctgccggcgc cgaaaaacct ggttgtttct gaagttaccg aagactctct gcgtctgtct      60

tggaccgcgc cggacgcggc gttcgactct ttcctgatcc agtaccagga atctgaaaaa     120

gttggtgaag cgatcaacct gaccgttccg ggttctgaac gttcttacga cctgaccggt     180

ctgaaaccgg gtaccgaata caccgtttct atctacggtg ttaaaggtgg tcaccgttct     240

aacccgctgt ctgcggaatt caccacc                                        267


<210> SEQ ID NO 60
<211> LENGTH: 7
<212> TYPE: PRT
<213> ORGANISM: Artificial sequence
<220> FEATURE:
<223> OTHER INFORMATION: linker

<400> SEQUENCE: 60

Thr Ser Gly Gly Gly Gly Ser
1               5


<210> SEQ ID NO 61
<211> LENGTH: 89
<212> TYPE: PRT
<213> ORGANISM: Artificial sequence
<220> FEATURE:
<223> OTHER INFORMATION: TCL15 library on tencon27 having randomized
      A-AB-B-BC-E surface
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (13)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
```

<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid

<400> SEQUENCE: 61

```
Leu Pro Ala Pro Lys Xaa Leu Xaa Val Xaa Xaa Val Xaa Xaa Xaa Xaa
1               5                   10                  15

Ala Xaa Leu Xaa Trp Xaa Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Xaa Tyr Xaa Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85
```

<210> SEQ ID NO 62
<211> LENGTH: 89
<212> TYPE: PRT
<213> ORGANISM: Artificial sequence
<220> FEATURE:
<223> OTHER INFORMATION: Fibcon library with randomized C-CD-F-FG surface
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(41)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (78)..(79)
<223> OTHER INFORMATION: Xaa can be any naturally occurring amino acid
<220> FEATURE:
<221> NAME/KEY: misc_feature
<222> LOCATION: (81)..(81)
<223> OTHER INFORMATION: Xaa can be any naturally occurring amino acid

<400> SEQUENCE: 62

```
Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Xaa
            20                  25                  30
```

-continued

```
Ile Xaa Tyr Xaa Pro Xaa Xaa Xaa Xaa Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Xaa Val Xaa Leu Xaa Ala Leu Lys Asp Asn Xaa Xaa Ser
65                  70                  75                  80

Xaa Pro Leu Val Gly Thr Gln Thr Thr
                85


<210> SEQ ID NO 63
<211> LENGTH: 9
<212> TYPE: PRT
<213> ORGANISM: Artificial sequence
<220> FEATURE:
<223> OTHER INFORMATION: C strand sequence of scaffold TP1KR9P61-A2

<400> SEQUENCE: 63

Asp Ser Phe Ala Ile Glu Tyr Phe Glu
1               5


<210> SEQ ID NO 64
<211> LENGTH: 9
<212> TYPE: PRT
<213> ORGANISM: Artificial sequence
<220> FEATURE:
<223> OTHER INFORMATION: C strand sequence of clone TP1KR9P62-A2

<400> SEQUENCE: 64

Asp Ser Phe Ala Ile Glu Tyr Ser Glu
1               5


<210> SEQ ID NO 65
<211> LENGTH: 9
<212> TYPE: PRT
<213> ORGANISM: Artificial sequence
<220> FEATURE:
<223> OTHER INFORMATION: C strand sequence of clone TP1KR9P62-D4

<400> SEQUENCE: 65

Asp Ser Phe Gly Ile Ile Tyr Phe Glu
1               5


<210> SEQ ID NO 66
<211> LENGTH: 9
<212> TYPE: PRT
<213> ORGANISM: Artificial sequence
<220> FEATURE:
<223> OTHER INFORMATION: C strand sequence of clone TP1KR9P62-E3

<400> SEQUENCE: 66

Asp Ser Phe Gly Ile Glu Tyr Phe Glu
1               5


<210> SEQ ID NO 67
<211> LENGTH: 6
<212> TYPE: PRT
<213> ORGANISM: Artificial sequence
<220> FEATURE:
<223> OTHER INFORMATION: CD loop of TP1KR9P61-A2

<400> SEQUENCE: 67

Asp Trp Trp Ser Gly Glu
1               5
```

-continued

<210> SEQ ID NO 68
<211> LENGTH: 6
<212> TYPE: PRT
<213> ORGANISM: Artificial sequence
<220> FEATURE:
<223> OTHER INFORMATION: CD loop of TP1KR9P62-A2

<400> SEQUENCE: 68

Asp Tyr Trp Leu Gly Glu
1               5

<210> SEQ ID NO 69
<211> LENGTH: 6
<212> TYPE: PRT
<213> ORGANISM: Artificial sequence
<220> FEATURE:
<223> OTHER INFORMATION: CD loop of TP1KR9P62-D4

<400> SEQUENCE: 69

Asp Trp Trp Ala Gly Glu
1               5

<210> SEQ ID NO 70
<211> LENGTH: 6
<212> TYPE: PRT
<213> ORGANISM: Artificial sequence
<220> FEATURE:
<223> OTHER INFORMATION: CD loop of TP1KR9P62-E3

<400> SEQUENCE: 70

Asp Tyr Trp Thr Gly Glu
1               5

<210> SEQ ID NO 71
<211> LENGTH: 10
<212> TYPE: PRT
<213> ORGANISM: Artificial sequence
<220> FEATURE:
<223> OTHER INFORMATION: F strand of TP1KR9P61-A2

<400> SEQUENCE: 71

Thr Glu Tyr Ala Val Ser Ile Arg Gly Val
1               5                   10

<210> SEQ ID NO 72
<211> LENGTH: 10
<212> TYPE: PRT
<213> ORGANISM: Artificial sequence
<220> FEATURE:
<223> OTHER INFORMATION: F strand of TP1KR9P61-A7

<400> SEQUENCE: 72

Thr Glu Tyr Ser Val Ser Ile Arg Gly Val
1               5                   10

<210> SEQ ID NO 73
<211> LENGTH: 10
<212> TYPE: PRT
<213> ORGANISM: Artificial sequence
<220> FEATURE:
<223> OTHER INFORMATION: TP1KR9P62-A2

<400> SEQUENCE: 73

Thr Glu Tyr Gly Val Ser Ile Arg Gly Val
1               5                   10

<210> SEQ ID NO 74

<211> LENGTH: 10
<212> TYPE: PRT
<213> ORGANISM: Artificial sequence
<220> FEATURE:
<223> OTHER INFORMATION: F strand of TP1KR9P62-C3

<400> SEQUENCE: 74

Thr Glu Tyr Ser Val Thr Ile Arg Gly Val
1 5 10

<210> SEQ ID NO 75
<211> LENGTH: 7
<212> TYPE: PRT
<213> ORGANISM: Artificial sequence
<220> FEATURE:
<223> OTHER INFORMATION: FG loop of TP1KR9P61-A2

<400> SEQUENCE: 75

Lys Gly Gly Met Pro Ser Ala
1 5

<210> SEQ ID NO 76
<211> LENGTH: 7
<212> TYPE: PRT
<213> ORGANISM: Artificial sequence
<220> FEATURE:
<223> OTHER INFORMATION: FG loop of TP1KR9P61-A7

<400> SEQUENCE: 76

Lys Gly Gly Tyr Pro Ser Ser
1 5

<210> SEQ ID NO 77
<211> LENGTH: 7
<212> TYPE: PRT
<213> ORGANISM: Artificial sequence
<220> FEATURE:
<223> OTHER INFORMATION: FG loop of TP1KR9P61-E2

<400> SEQUENCE: 77

Lys Gly Gly Met Pro Ser Pro
1 5

<210> SEQ ID NO 78
<211> LENGTH: 7
<212> TYPE: PRT
<213> ORGANISM: Artificial sequence
<220> FEATURE:
<223> OTHER INFORMATION: FG loop of TP1KR9P61-G4

<400> SEQUENCE: 78

Lys Gly Gly Tyr Pro Ser Ala
1 5

<210> SEQ ID NO 79
<211> LENGTH: 7
<212> TYPE: PRT
<213> ORGANISM: Artificial sequence
<220> FEATURE:
<223> OTHER INFORMATION: FG loop of TP1KR9P62-A2

<400> SEQUENCE: 79

Lys Gly Gly Tyr Pro Ser Pro
1 5

<210> SEQ ID NO 80
<211> LENGTH: 7

<212> TYPE: PRT
<213> ORGANISM: Artificial sequence
<220> FEATURE:
<223> OTHER INFORMATION: FG loop of TP1KR9P62-C3

<400> SEQUENCE: 80

Lys Gly Gly Pro Pro Ser Ser
1 5

<210> SEQ ID NO 81
<211> LENGTH: 7
<212> TYPE: PRT
<213> ORGANISM: Artificial sequence
<220> FEATURE:
<223> OTHER INFORMATION: FG loop of TP1KR9P62-C6

<400> SEQUENCE: 81

Lys Gly Gly Tyr Pro Ser Ser
1 5

<210> SEQ ID NO 82
<211> LENGTH: 7
<212> TYPE: PRT
<213> ORGANISM: Artificial sequence
<220> FEATURE:
<223> OTHER INFORMATION: FG loop of TP1KR9P62-D4

<400> SEQUENCE: 82

Lys Gly Gly Pro Pro Ser Arg
1 5

<210> SEQ ID NO 83
<211> LENGTH: 7
<212> TYPE: PRT
<213> ORGANISM: Artificial sequence
<220> FEATURE:
<223> OTHER INFORMATION: FG loop of TP1KR9P62-D8

<400> SEQUENCE: 83

Lys Gly Gly Leu Ala Ser Pro
1 5

<210> SEQ ID NO 84
<211> LENGTH: 7
<212> TYPE: PRT
<213> ORGANISM: Artificial sequence
<220> FEATURE:
<223> OTHER INFORMATION: FG loop of TP1KR9P62-H10

<400> SEQUENCE: 84

Lys Gly Gly His Pro Ser Val
1 5

<210> SEQ ID NO 85
<211> LENGTH: 90
<212> TYPE: PRT
<213> ORGANISM: Artificial sequence
<220> FEATURE:
<223> OTHER INFORMATION: mIL-17A binding scaffold TP1KR9P61-A2

<400> SEQUENCE: 85

Met Leu Pro Ala Pro Lys Asn Leu Val Val Ser Arg Val Thr Glu Asp
1 5 10 15

Ser Ala Arg Leu Ser Trp Thr Ala Pro Asp Ala Ala Phe Asp Ser Phe
20 25 30

Ala Ile Glu Tyr Phe Glu Asp Trp Trp Ser Gly Glu Ala Ile Val Leu

```
        35                  40                  45

Thr Val Pro Gly Ser Glu Arg Ser Tyr Asp Leu Thr Gly Leu Lys Pro
    50                  55                  60

Gly Thr Glu Tyr Ala Val Ser Ile Arg Gly Val Lys Gly Gly Met Pro
65                  70                  75                  80

Ser Ala Pro Leu Ser Ala Ile Phe Thr Thr
                85                  90


<210> SEQ ID NO 86
<211> LENGTH: 90
<212> TYPE: PRT
<213> ORGANISM: Artificial sequence
<220> FEATURE:
<223> OTHER INFORMATION: mIL-17A binding scaffold TP1KR9P61-A7

<400> SEQUENCE: 86

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Asp Trp Trp Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Ser Ile Arg Gly Val Lys Gly Gly Tyr Pro
65                  70                  75                  80

Ser Ser Pro Leu Ser Ala Ile Phe Thr Thr
                85                  90


<210> SEQ ID NO 87
<211> LENGTH: 90
<212> TYPE: PRT
<213> ORGANISM: Artificial sequence
<220> FEATURE:
<223> OTHER INFORMATION: mIL-17A binding scaffold TP1KR9P61-E2

<400> SEQUENCE: 87

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Asp Trp Trp Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Ser Ile Arg Gly Val Lys Gly Gly Met Pro
65                  70                  75                  80

Ser Pro Pro Leu Ser Ala Ile Phe Thr Thr
                85                  90


<210> SEQ ID NO 88
<211> LENGTH: 90
<212> TYPE: PRT
<213> ORGANISM: Artificial sequence
<220> FEATURE:
<223> OTHER INFORMATION: mIL-17A binding scaffold TP1KR9P61-G4

<400> SEQUENCE: 88

Met Leu Pro Ala Pro Lys Asn Leu Val Val Ser Arg Val Thr Glu Asp
1               5                   10                  15
```

```
Ser Ala Arg Leu Ser Trp Thr Ala Pro Asp Ala Ala Phe Asp Ser Phe
            20                  25                  30

Ala Ile Glu Tyr Phe Glu Asp Trp Trp Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Ser Ile Arg Gly Val Lys Gly Gly Tyr Pro
65                  70                  75                  80

Ser Ala Pro Leu Ser Ala Ile Phe Thr Thr
                85                  90
```

<210> SEQ ID NO 89
<211> LENGTH: 90
<212> TYPE: PRT
<213> ORGANISM: Artificial sequence
<220> FEATURE:
<223> OTHER INFORMATION: mIL-17A binding scaffold TP1KR9P62-A2

<400> SEQUENCE: 89

```
Met Leu Pro Ala Leu Lys Asn Leu Val Val Ser Arg Val Thr Glu Asp
1               5                   10                  15

Ser Ala His Leu Ser Trp Thr Ala Pro Asp Ala Ala Phe Asp Ser Phe
            20                  25                  30

Ala Ile Glu Tyr Ser Glu Asp Tyr Trp Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Ser Ile Arg Gly Val Lys Gly Gly Tyr Pro
65                  70                  75                  80

Ser Pro Pro Leu Ser Ala Ile Phe Thr Thr
                85                  90
```

<210> SEQ ID NO 90
<211> LENGTH: 90
<212> TYPE: PRT
<213> ORGANISM: Artificial sequence
<220> FEATURE:
<223> OTHER INFORMATION: mIL-17A binding scaffold TP1KR9P62-C3

<400> SEQUENCE: 90

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Asp Trp Trp Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Thr Ile Arg Gly Val Lys Gly Gly Pro Pro
65                  70                  75                  80

Ser Ser Pro Leu Ser Ala Ile Phe Thr Thr
                85                  90
```

<210> SEQ ID NO 91
<211> LENGTH: 90
<212> TYPE: PRT
<213> ORGANISM: Artificial sequence
<220> FEATURE:
<223> OTHER INFORMATION: mIL-17A binding scaffold TP1KR9P62-C6

<400> SEQUENCE: 91

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Asp Trp Trp Ser Gly Glu Ala Ile Val Leu
        35                  40                  45

Thr Val Pro Gly Ser Glu Arg Ser Cys Asp Leu Thr Gly Leu Lys Pro
    50                  55                  60

Gly Thr Glu Tyr Ser Val Thr Ile Arg Gly Val Lys Gly Gly Tyr Pro
65                  70                  75                  80

Ser Ser Pro Leu Ser Ala Ile Phe Thr Thr
                85                  90

<210> SEQ ID NO 92
<211> LENGTH: 89
<212> TYPE: PRT
<213> ORGANISM: Artificial sequence
<220> FEATURE:
<223> OTHER INFORMATION: mIL-17A binding scaffold TP1KR9P62-D3

<400> SEQUENCE: 92

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Asp Trp Trp Ser Gly Glu Ala Ile Val Leu
        35                  40                  45

Thr Val Pro Gly Ser Glu Arg Ser Tyr Asp Leu Thr Leu Lys Pro Gly
    50                  55                  60

Thr Glu Tyr Ser Val Ser Ile Arg Gly Val Lys Gly Gly Tyr Pro Ser
65                  70                  75                  80

Ser Pro Leu Ser Ala Ile Phe Thr Thr
                85

<210> SEQ ID NO 93
<211> LENGTH: 90
<212> TYPE: PRT
<213> ORGANISM: Artificial sequence
<220> FEATURE:
<223> OTHER INFORMATION: mIL-17A binding scaffold TP1KR9P62-D4

<400> SEQUENCE: 93

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ile Tyr Phe Glu Asp Trp Trp Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Ser Ile Arg Gly Val Lys Gly Gly Pro Pro
65                  70                  75                  80

Ser Arg Pro Leu Ser Ala Ile Phe Thr Thr
                85                  90

<210> SEQ ID NO 94

<211> LENGTH: 90
<212> TYPE: PRT
<213> ORGANISM: Artificial sequence
<220> FEATURE:
<223> OTHER INFORMATION: mIL-17A binding scaffold TP1KR9P62-D8

<400> SEQUENCE: 94

Met Leu Pro Ala Pro Lys Asn Leu Val Val Ser Arg Val Thr Glu Asp
1 5 10 15

Ser Ala Arg Leu Ser Trp Thr Ala Pro Asp Ala Ala Phe Asp Ser Phe
20 25 30

Ala Ile Glu Tyr Phe Glu Asp Trp Trp Ser Gly Glu Ala Ile Val Leu
35 40 45

Thr Val Pro Gly Ser Glu Arg Ser Tyr Asp Leu Thr Gly Leu Lys Pro
50 55 60

Gly Thr Glu Tyr Gly Val Ser Ile Arg Gly Val Lys Gly Gly Leu Ala
65 70 75 80

Ser Pro Pro Leu Ser Ala Ile Phe Thr Thr
85 90

<210> SEQ ID NO 95
<211> LENGTH: 90
<212> TYPE: PRT
<213> ORGANISM: Artificial sequence
<220> FEATURE:
<223> OTHER INFORMATION: mIL-17A binding scaffold TP1KR9P62-E3

<400> SEQUENCE: 95

Met Leu Pro Ala Pro Lys Asn Leu Val Val Ser Arg Val Thr Glu Asp
1 5 10 15

Ser Ala Arg Leu Ser Trp Thr Ala Pro Asp Ala Ala Phe Asp Ser Phe
20 25 30

Gly Ile Glu Tyr Phe Glu Asp Tyr Trp Thr Gly Glu Ala Ile Val Leu
35 40 45

Thr Val Pro Gly Ser Glu Arg Ser Tyr Asp Leu Thr Gly Leu Lys Pro
50 55 60

Gly Thr Glu Tyr Ala Val Ser Ile Arg Gly Val Lys Gly Gly Tyr Pro
65 70 75 80

Ser Ala Pro Leu Ser Ala Ile Phe Thr Thr
85 90

<210> SEQ ID NO 96
<211> LENGTH: 90
<212> TYPE: PRT
<213> ORGANISM: Artificial sequence
<220> FEATURE:
<223> OTHER INFORMATION: mIL-17A binding scaffold TP1KR9P62-H10

<400> SEQUENCE: 96

Met Leu Pro Ala Pro Lys Asn Leu Val Val Ser Arg Val Thr Glu Asp
1 5 10 15

Ser Ala Arg Leu Ser Trp Thr Ala Pro Asp Ala Ala Phe Asp Ser Phe
20 25 30

Ala Ile Glu Tyr Phe Glu Asp Trp Trp Ser Gly Glu Ala Ile Val Leu
35 40 45

Thr Val Pro Gly Ser Glu Arg Ser Tyr Asp Leu Thr Gly Leu Lys Pro
50 55 60

Gly Thr Glu Tyr Ser Val Ser Ile Arg Gly Val Lys Gly Gly His Pro
65 70 75 80

```
Ser Val Pro Leu Ser Ala Ile Phe Thr Thr
                85                  90


<210> SEQ ID NO 97
<211> LENGTH: 94
<212> TYPE: PRT
<213> ORGANISM: homo sapiens

<400> SEQUENCE: 97

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90


<210> SEQ ID NO 98
<211> LENGTH: 94
<212> TYPE: PRT
<213> ORGANISM: Artificial sequence
<220> FEATURE:
<223> OTHER INFORMATION: FN10 based scaffold library with randomized
      C-CD-F-FG surface
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(42)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (83)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid

<400> SEQUENCE: 98

Val Ser Asp Val Pro Arg Asp Leu Glu Val Val Ala Ala Thr Pro Thr
1               5                   10                  15
```

-continued

```
Ser Leu Leu Ile Ser Trp Asp Ala Pro Ala Val Thr Val Arg Tyr Tyr
            20                  25                  30

Xaa Ile Xaa Tyr Xaa Glu Xaa Xaa Xaa Xaa Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Xaa Ile Xaa Val Xaa Ala Val Thr Gly Arg Gly Asp
65                  70                  75                  80

Ser Pro Xaa Xaa Ser Xaa Pro Ile Ser Ile Asn Tyr Arg Thr
                85                  90
```

```
<210> SEQ ID NO 99
<211> LENGTH: 88
<212> TYPE: PRT
<213> ORGANISM: Artificial sequence
<220> FEATURE:
<223> OTHER INFORMATION: TN3 based scaffodl library with randomized
      C-CD-F-FG surface
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (37)..(40)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (77)..(78)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid

<400> SEQUENCE: 99

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Xaa Leu
            20                  25                  30

Xaa Tyr Xaa Ile Xaa Xaa Xaa Xaa Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Xaa Val Xaa Leu Xaa Ser Arg Arg Gly Asp Xaa Xaa Ser Xaa
65                  70                  75                  80

Pro Ala Lys Glu Thr Phe Thr Thr
                85
```

<210> SEQ ID NO 100
<211> LENGTH: 270
<212> TYPE: DNA
<213> ORGANISM: Artificial sequence
<220> FEATURE:
<223> OTHER INFORMATION: cDNA encoding tencon27

<400> SEQUENCE: 100
atgctgccgg cgccgaaaaa cctggttgtt tctcgtgtta ccgaagactc tgcgcgtctg 60
tcttggaccg cgccggacgc ggcgttcgac tctttcctga tccagtacca ggaatctgaa 120
aaagttggtg aagcgatcgt tctgaccgtt ccgggttctg aacgttctta cgacctgacc 180
ggtctgaaac cgggtaccga atacaccgtt tctatctacg gtgttaaagg tggtcaccgt 240
tctaacccgc tgtctgcgat cttcaccacc 270

<210> SEQ ID NO 101
<211> LENGTH: 270
<212> TYPE: DNA
<213> ORGANISM: Artificial sequence
<220> FEATURE:
<223> OTHER INFORMATION: cDNA encoding TCL14 library
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (99)..(99)
<223> OTHER INFORMATION: s is c or g
<220> FEATURE:
<221> NAME/KEY: misc_feature
<222> LOCATION: (103)..(104)
<223> OTHER INFORMATION: n is a, c, g, or t
<220> FEATURE:
<221> NAME/KEY: misc_feature
<222> LOCATION: (105)..(105)
<223> OTHER INFORMATION: s is c or g
<220> FEATURE:
<221> NAME/KEY: misc_feature
<222> LOCATION: (109)..(110)
<223> OTHER INFORMATION: n is a, c, g, or t
<220> FEATURE:
<221> NAME/KEY: misc_feature
<222> LOCATION: (111)..(111)
<223> OTHER INFORMATION: s is c or g
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (117)..(117)
<223> OTHER INFORMATION: s is c or g
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (120)..(120)
<223> OTHER INFORMATION: s is c or g
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (123)..(123)
<223> OTHER INFORMATION: s is c or g
<220> FEATURE:
<221> NAME/KEY: misc_feature
<222> LOCATION: (124)..(125)

-continued

```
<223> OTHER INFORMATION: n is a, c, g, or t
<220> FEATURE:
<221> NAME/KEY: misc_feature
<222> LOCATION: (126)..(126)
<223> OTHER INFORMATION: s is c or g
<220> FEATURE:
<221> NAME/KEY: misc_feature
<222> LOCATION: (205)..(206)
<223> OTHER INFORMATION: n is a, c, g, or t
<220> FEATURE:
<221> NAME/KEY: misc_feature
<222> LOCATION: (207)..(207)
<223> OTHER INFORMATION: s is c or g
<220> FEATURE:
<221> NAME/KEY: misc_feature
<222> LOCATION: (211)..(212)
<223> OTHER INFORMATION: n is a, c, g, or t
<220> FEATURE:
<221> NAME/KEY: misc_feature
<222> LOCATION: (213)..(213)
<223> OTHER INFORMATION: s is c or g
<220> FEATURE:
<221> NAME/KEY: misc_feature
<222> LOCATION: (217)..(218)
<223> OTHER INFORMATION: n is a, c, g, or t
<220> FEATURE:
<221> NAME/KEY: misc_feature
<222> LOCATION: (219)..(219)
<223> OTHER INFORMATION: s is c or g
<220> FEATURE:
<221> NAME/KEY: misc_feature
<222> LOCATION: (235)..(236)
<223> OTHER INFORMATION: n is a, c, g, or t
<220> FEATURE:
<221> NAME/KEY: misc_feature
<222> LOCATION: (237)..(237)
<223> OTHER INFORMATION: s is c or g
<220> FEATURE:
<221> NAME/KEY: misc_feature
<222> LOCATION: (238)..(239)
<223> OTHER INFORMATION: n is a, c, g, or t
<220> FEATURE:
<221> NAME/KEY: misc_feature
<222> LOCATION: (240)..(240)
<223> OTHER INFORMATION: s is c or g
<220> FEATURE:
<221> NAME/KEY: misc_feature
<222> LOCATION: (244)..(245)
<223> OTHER INFORMATION: n is a, c, g, or t
<220> FEATURE:
<221> NAME/KEY: misc_feature
<222> LOCATION: (246)..(246)
<223> OTHER INFORMATION: s is c or g

<400> SEQUENCE: 101

atgctgccgg cgccgaaaaa cctggttgtt tctcgtgtta ccgaagactc tgcgcgtctg     60

tcttggaccg cgccggacgc ggcgttcgac tctttcnnsa tcnnstacnn sgaannsnns    120

nnsnnsggtg aagcgatcgt tctgaccgtt ccgggttctg aacgttctta cgacctgacc    180

ggtctgaaac cgggtaccga atacnnsgtt nnsatcnnsg gtgttaaagg tggtnnsnns    240

tctnnsccgc tgtctgcgat cttcaccacc                                     270
```